(12) United States Patent
Bolli et al.

(10) Patent No.: US 7,981,924 B2
(45) Date of Patent: Jul. 19, 2011

(54) THIOPHENE DERIVATIVES

(75) Inventors: Martin Bolli, Allschwil (CH); David Lehmann, Basel (CH); Boris Mathys, Pratteln (CH); Claus Mueller, Weil Am Rhein (DE); Oliver Nayler, Arlesheim (CH); Beat Steiner, Battwil (CH); Jörg Velker, Huningue (FR)

(73) Assignee: Actelion Pharmaceuticals Ltd., Allschwil (CH)

( * ) Notice: Subject to any disclaimer, the term of this patent is extended or adjusted under 35 U.S.C. 154(b) by 392 days.

(21) Appl. No.: 12/094,736

(22) PCT Filed: Nov. 22, 2006

(86) PCT No.: PCT/IB2006/054388
§ 371 (c)(1),
(2), (4) Date: May 22, 2008

(87) PCT Pub. No.: WO2007/060626
PCT Pub. Date: May 31, 2007

(65) Prior Publication Data
US 2008/0300294 A1 Dec. 4, 2008

(30) Foreign Application Priority Data
Nov. 23, 2005 (WO) .................. PCT/IB2005/053882

(51) Int. Cl.
A61K 31/38 (2006.01)
C07D 333/00 (2006.01)
(52) U.S. Cl. ......................................... 514/443; 549/57
(58) Field of Classification Search .................. 514/443; 549/57
See application file for complete search history.

(56) References Cited

U.S. PATENT DOCUMENTS

| | | | |
|---|---|---|---|
| 7,605,269 B2 | 10/2009 | Bolli et al. | |
| 7,750,040 B2 | 7/2010 | Bolli et al. | |
| 2004/0058894 A1 | 3/2004 | Doherty et al. | |
| 2008/0194670 A1 | 8/2008 | Bolli et al. | |
| 2009/0005421 A1 | 1/2009 | Bolli et al. | |
| 2010/0075946 A1 | 3/2010 | Bolli et al. | |
| 2010/0204198 A1 | 8/2010 | Bolli et al. | |

FOREIGN PATENT DOCUMENTS

| | | |
|---|---|---|
| EP | 310321 A2 | 9/1988 |
| EP | 0 476646 | 3/1992 |
| GB | 2 336 588 | 10/1999 |
| WO | WO-91/15583 A1 | 10/1991 |
| WO | WO-99/46277 A1 | 9/1999 |
| WO | WO 03062248 | 7/2003 |
| WO | WO 2005/014525 | 2/2005 |
| WO | WO 2005/058848 | 6/2005 |
| WO | WO-2006/100631 | 9/2006 |
| WO | WO 2006/131336 | 12/2006 |
| WO | WO 2007/085451 | 8/2007 |

OTHER PUBLICATIONS

J.P. Konopelski, et al., "Carbanion Stabilization by Distal Silyloxy Groups. Origin of the High Diastereoselectivity in the Formation of Quaternary Centers with Aryllead(IV) Triacetate Reagents," Organic Letters 4 (2002), pp. 4121-4124.
C. Wiles, et al., "The regioselective preparation of 1,3-diketones," Tetrahedron Letters 43 (2002), pp. 2945-2948.
R. Faure, et al., "Synthesis, $^1$H and $^{13}$C NMR Study of Pyrazoles Derived From Chiral Cyclohexanones (3-Methylcyclohexanone, Menthone, Pulegone, Dihydrocarvone and Carvone)," Heterocycles 57 (2002), pp. 307-316.
M. Hammadi, et al., "Clay Catalysis: Storks's Alkylation and Acylation of Cyclohexanone Without Isolation of Enamine," Synthetic Communications 26 (1996), pp. 2901-2904.
M.E. Flaugh, et al., "Acid-Catalyzed Annelation of α-Alkyl Aldehydes and α,β-Unsaturated Ketones. A One-Pot Synthesis of 4,4-Dimethyl-2-cyclohexen-1-one," Journal of Organic Chemistry 45 (1980), pp. 5399-5400.
N.R. Natale, et al., "An Efficient, General Synthesis of Spiroalkenes and Related Derivatives[1]," Organic Preparations and Procedures International 9 (1977), pp. 103-108.
L.M. Rice, et al., "Spirans XX. Synthesis of 8,8-Dialkylazaspiro [4.5] decanes and 9,9-Dialkylazaspiro [5.5] undecanes," Journal of Heterocyclic Chemistry 10 (1973), pp. 731-735.
W.-D. Liu, et al., "Synthesis Of 2,5-Disubstituted Thienosultines and Their Thermal Reactions With Dienophiles And Neucleophiles," Journal of Organic Chemistry 67 (2002), pp. 9267-9275.
D.W. Knight, et al., "Formation and Reactivity of Dianions Derived From 2- and 3-Thiophencarboxylic Acids," Tetrahedron Letters 21 (1980), pp. 5051-5054.
R. Raap, "Preparation of 5-Aminomethyl-2-thienylacetic Acid from 1-Methylthio-2-(2'-thienyl)ethyne," Canadian Journal of Chemistry 49 (1971), pp. 2155-2157.
D.E. Nichols, et al., "1-(2,5-Dimethoxy-4(trifluoromethyl)phenyl)-2-aminopropane: A Potent Serotonin 5-HT 2A/2C Agonist," J. Med. Chem. 37 (1994), pp. 4346-4351.
F. Orsini, et al., "Pd(0)-Mediated Cross-Coupling of Reformatsky Reagents With Vinyl- and Aryl Triflates," Synthetic Comm. 17 (1987), pp. 1389-1402.
H. Kotsuki, et al., "An Efficient Procedure for Palladium-Catalyzed Hydroformlyation of Aryl/Enol Triflates," Synthesis 1996, pp. 470-472.
V.P. Baillargeon, et al., "Palladium-Catalyzed Formylation of Organic Halides with Carbon Monoxide and Tin Hydride," J. Am. Chem. Soc. 108 (1986), pp. 452-461.
M.J. Gomez-Escalonilla, et al., "Synthesis of dumbbell-shaped bis-(pyrazolino[60]fullerene)-oligophenylenevinylene derivatives," Tetrahederon Letters 43 (2002), pp. 7507-7511.
Y. Li, et al., "High Enantioselective Cyanosilylation of Aldehydes Catalyzed by Novel β-Amino Alcohol-Titanium Complexes," J. Org. Chem. 69 (2004), pp. 7910-7913.
G. Battistuzzi, et al., "An Efficient Palladium-Catalyzed Synthesis of Cinnamaldehydes from Acrolein Diethyl Acetal and Aryl Iodides and Bromides," Org. Lett. 5 (2003), pp. 777-780.

(Continued)

Primary Examiner — Taylor Victor Oh
(74) Attorney, Agent, or Firm — Hoxie & Associates LLC

(57) ABSTRACT

The invention relates to novel thiophene derivatives, their preparation and their use as pharmaceutically active compounds. Said compounds particularly act as immunosuppressive agents.

34 Claims, No Drawings

OTHER PUBLICATIONS

N.J. Lawrence, et al., "The asymmetric synthesis of β-aryl-α-hydroxy esters from β-aryl-α,β-dihydroxy esters," Tetrahedron 58 (2002), pp. 613-619.

D. J. Wardrop, et al., "Total synthesis of (−) dysibetaine via a nitrenium ion cyclization—dienone cleavage strategy," Chem. Comm. 2004, pp. 1230-1231.

T. Azemi, et al., "Transformation of 1,5- and 1,6-dienes to carbocycles by hydrozirconation and oxidation with cerium (IV) compounds," Tetrahedron 60 (2004), pp. 1339-1344.

A. Krasovskiy, et al., "A LiCl-Mediated Br/Mg Exchange Reaction for the Preparation of Functionalized Aryl- and Heteroarylmagnesium Compounds from Organic Bromides," Angew. Chem. Int. Ed. 43 (2004), pp. 3333-3336.

T.P. Zabawa, et al., "Copper (II) Acetate Promoted Intramolecular Diamination of Unactivated Olefins," J. Am. Chem. Soc. 127 (2005), pp. 11250-11251.

W.P. Gallagher, et al., "PMHS-Mediated Couplings of Alkynes or Benzothiazoles with Various Electrophiles: Application to the Synthesis of (—)-Akolactone A," J. Org. Chem. 68 (2003), pp. 6775-6779.

A.-Y. Peng, et al., "The Synthesis of Phosphaisocoumarins by Cu(I)-Catalyzed Intramolecular Cyclization of o-Ethynylphenylphosphonic Acid Monoesters," J. Am. Chem. Soc. 125 (2003), pp. 15006-15007.

R.A. Fernandes, et al. "Asymmetric dihydroxylation and regioselective C-3 indole coupling routes to the anticoccidial antibiotics (+)-diolmycine A2," Tetrahedron 58 (2002), pp. 1223-1227.

Lakhvich et al., Organic Chemistry Journal, vol. 25, Part 12, pp. 2541-2549 (1989) (w/English translation of same).

Aust et al., J. Prakt. Chem., vol. 341, No. 6, pp. 523-528 (1999) w/English translation of same).

T. Hla, et al., "An Abundant Transcript Induced in Differentiating Human Endothelial Cells Encodes a Polypeptide with Structural Similarities to G-protein-coupled Receptors," J. Biol Chem. 265 (1990), pp. 9308-9313.

P.L. Gould, "Salt selection for basic drugs," Int. J. Pharm. 33 (1986), pp. 201-217.

Mark Gibson, Editor, Pharmaceutical Preformulation and Formulation, IHS Health Group, Englewood, CO, USA, 2001.

A.R. Gennaro, Remington: The Science and Practice of Pharmacy, 20th Edition, Philadelphia College of Pharmacy and Science, Jun. 2003.

M. Mentzel, et al., "N-Methoxy-N-methylamides (Weinreb Amides) in Modern Organic Synthesis," Journal Fuer Praktische Chemie/Chemiker-Zeitung 339 (1997), pp. 517-524.

J. Singh, et al., "The Growing Synthetic Utility of Weinreb's Amide," Journal fuer Praktische Chemie (Weinheim, Germany) 342 (2000), pp. 340-347.

V.K. Khlestkin, et al., "Recent Advances in the Application of N,O-Dialkylhydroxylamines in Organic Chemistry," Current Organic Chemistry 7 (2003), pp. 967-993.

R.E. Mewshaw, et al., "Vilsmeier Reagents: Preparation of β-Halo-α,β-Unsaturated Ketones," Tetrahedron Lett. 30 (1989), pp. 3753-3756.

C. Kashima, et al., "Preparation of 2,6-Bis (*l*-menthopyrzol-3-yl)pyridines and their Catalytic Activity for Asymmetric Diels Alder Reaction," Journal of Heterocyclic Chemistry 40 (2003), pp. 773-782.

I. Yavari, et al., "A new synthesis of highly functionalized 2*H*-pyran derivatives," Tetrahedron 59 (2003), pp. 2001-2005.

THIOPHENE DERIVATIVES

FIELD OF THE INVENTION

The present invention relates to S1P1/EDG1 receptor agonists of Formula (I) and their use as active ingredients in the preparation of pharmaceutical compositions. The invention also concerns related aspects including processes for the preparation of the compounds, pharmaceutical compositions containing a compound of the Formula (I), and their use as compounds improving vascular function and as immunomodulating agents, either alone or in combination with other active compounds or therapies. A further aspect of the invention relates to novel compounds of Formulae (II) and (III) that serve as intermediates to prepare compounds of Formula (I).

BACKGROUND OF THE INVENTION

The human immune system is designed to defend the body against foreign micro-organisms and substances that cause infection or disease. Complex regulatory mechanisms ensure that the immune response is targeted against the intruding substance or organism and not against the host. In some cases, these control mechanisms are unregulated and autoimmune responses can develop. A consequence of the uncontrolled inflammatory response is severe organ, cell, tissue or joint damage. With current treatment, the whole immune system is usually suppressed and the body's ability to react to infections is also severely compromised. Typical drugs in this class include azathioprine, chlorambucil, cyclophosphamide, cyclosporin, or methotrexate. Corticosteroids which reduce inflammation and suppress the immune response, may cause side effects when used in long term treatment. Nonsteroidal anti-infammatory drugs (NSAIDs) can reduce pain and inflammation, however, they exhibit considerable side effects. Alternative treatments include agents that activate or block cytokine signaling. Orally active compounds with immunomodulating properties, without compromising immune responses and with reduced side effects would significantly improve current treatments of uncontrolled inflammatory disease.

In the field of organ transplantation the host immune response must be suppressed to prevent organ rejection. Organ transplant recipients can experience some rejection even when they are taking immunosuppressive drugs. Rejection occurs most frequently in the first few weeks after transplantation, but rejection episodes can also happen months or even years after transplantation. Combinations of up to three or four medications are commonly used to give maximum protection against rejection while minimizing side effects. Current standard drugs used to treat the rejection of transplanted organs interfere with discrete intracellular pathways in the activation of T-type or B-type white blood cells. Examples of such drugs are cyclosporin, daclizumab, basiliximab, everolimus, or FK506, which interfere with cytokine release or signaling; azathioprine or leflunomide, which inhibit nucleotide synthesis; or 15-deoxyspergualin, an inhibitor of leukocyte differentiation.

The beneficial effects of broad immunosuppressive therapies relate to their effects; however, the generalized immunosuppression which these drugs produce diminishes the immune system's defense against infection and malignancies. Furthermore, standard immunosuppressive drugs are often used at high dosages and can cause or accelerate organ damage.

DESCRIPTION OF THE INVENTION

The present invention provides novel compounds of Formula (I) that are agonists for the G protein-coupled receptor S1P1/EDG1 and have a powerful and long-lasting immunosuppressive effect which is achieved by reducing the number of circulating and infiltrating T- and B-lymphocytes, without affecting their maturation, memory, or expansion. The reduction of circulating T-/B-lymphocytes as a result of S1P1/EDG1 agonism, possibly in combination with the observed improvement of endothelial cell layer function associated with S1P1/EDG1 activation, makes such compounds useful to treat uncontrolled inflammatory disease and to improve vascular functionality.

The compounds of the present invention can be utilized alone or in combination with standard drugs inhibiting T-cell activation, to provide a new immunosuppressive therapy with a reduced propensity for infections when compared to standard immunosuppressive therapy. Furthermore, the compounds of the present invention can be used in combination with reduced dosages of traditional immunosuppressant therapies, to provide on the one hand effective immunosuppressive activity, while on the other hand reducing end organ damage associated with higher doses of standard immunosuppressive drugs. The observation of improved endothelial cell layer function associated with S1P1/EDG1 activation provides additional benefits of compounds to improve vascular function.

The nucleotide sequence and the amino acid sequence for the human S1P1/EDG1 receptor are known in the art and are published in e.g.: Hla, T., and Maciag, T. *J. Biol. Chem.* 265 (1990), 9308-9313; WO 91/15583 published 17 Oct. 1991; WO 99/46277 published 16 Sep. 1999. The potency and efficacy of the compounds of Formula (I) are assessed using a GTPγS assay to determine $EC_{50}$ values and by measuring the circulating lymphocytes in the rat after oral administration, respectively (see in Examples).

i) The invention relates to novel thiophenes of the Formula (I),

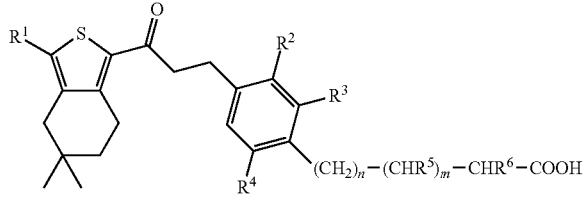

Formula (I)

wherein
$R^1$ represents methyl, trifluoromethyl, or ethyl;
$R^2$ represents hydrogen, $C_{1-4}$-alkyl, methoxy, or halogen;
$R^3$ represents hydrogen, $C_{1-4}$-alkyl, $C_{1-4}$-alkoxy, or halogen;
$R^4$ represents hydrogen, $C_{1-4}$-alkyl, or halogen;
$R^5$ represents hydrogen;
$R^6$ represents hydrogen or hydroxy;
in case $R^6$ represents hydroxy, $R^5$ can in addition represent hydroxy;
n represents 0;
m represents 0 or 1; and
in case m represents 1, n can in addition represent 1;
and salts as well as solvent complexes of such compounds.

The general terms used hereinbefore and hereinafter preferably have, within this disclosure, the following meanings, unless otherwise indicated:

Where the plural form is used for compounds, salts, pharmaceutical compositions, diseases and the like, this is intended to mean also a single compound, salt, or the like.

Any reference hereinbefore or hereinafter to a compound of Formula (I), (II) or (III) is to be understood as referring also to enantiomers, mixtures of enantiomers such as racemates, diastereomers, mixtures of diastereomers, and mixtures of enantiomers and diastereomers such as diastereomeric racemates, as well as salts (especially pharmaceutically acceptable salts) and solvent complexes (including hydrates) of such compounds, and morphological forms, as appropriate and expedient.

The term $C_{1-4}$-alkyl, alone or in combination with other groups, means saturated, branched or preferably straight chain groups with one to four carbon atoms, preferably one to three carbon atoms. Examples of $C_{1-4}$-alkyl groups are methyl, ethyl, n-propyl, iso-propyl, n-butyl, iso-butyl, sec-butyl, and tert-butyl.

The term $C_{1-4}$-alkoxy means an R—O group, wherein R is a $C_{1-4}$-alkyl. Preferred examples of $C_{1-4}$-alkoxy groups are methoxy, ethoxy, propoxy, and iso-propoxy.

The term halogen means fluoro, chloro, bromo or iodo, preferably fluoro or chloro.

Salts are preferably the pharmaceutically acceptable salts of the compounds of Formula (I).

Salt-forming groups are groups or radicals having basic or acidic properties. Compounds having at least one basic group or at least one basic radical, for example amino, a secondary amino group not forming a peptide bond or a pyridyl radical, may form acid addition salts, for example with inorganic acids. When several basic groups are present mono- or poly-acid addition salts may be formed.

Compounds having acidic groups, such as a carboxy group or a phenolic hydroxy group, may form metal or ammonium salts, such as alkali metal or alkaline earth metal salts, for example sodium, potassium, magnesium or calcium salts, or ammonium salts with ammonia or suitable organic amines, such as tertiary monoamines, for example triethylamine or tri-(2-hydroxyethyl)-amine, or heterocyclic bases, for example N-ethyl-piperidine or N,N'-dimethylpiperazine. Mixtures of salts are possible.

Compounds having both acidic and basic groups can form internal salts.

For the purposes of isolation or purification, as well as in the case of compounds that are used further as intermediates, it is also possible to use pharmaceutically unacceptable salts, e.g. the picrates. Only pharmaceutically acceptable, non-toxic salts may be used for therapeutic purposes, however, and those salts are therefore preferred.

The expression pharmaceutically acceptable salts encompasses either salts with inorganic acids or organic acids like hydrochloric acid, hydrobromic acid, hydroiodic acid, sulfuric acid, sulfamic acid, phosphoric acid, nitric acid, phosphorous acid, nitrous acid, citric acid, formic acid, acetic acid, oxalic acid, maleic acid, lactic acid, tartaric acid, fumaric acid, benzoic acid, mandelic acid, cinnamic acid, palmoic acid, stearic acid, glutamic acid, aspartic acid, methanesulfonic acid, ethanesulfonic acid, ethanedisulfonic acid, p-toluenesulfonic acid, salicylic acid, succinic acid, trifluoroacetic acid, and the like that are non toxic to living organisms or, in case the compound of Formula (I) is acidic in nature, with an inorganic base like an alkali or earth alkali base, e.g. sodium hydroxide, potassium hydroxide, calcium hydroxide and the like. For other examples of pharmaceutically acceptable salts, reference can be made to "Salt selection for basic drugs", *Int. J. Pharm.* (1986), 33, 201-217.

The compounds of the Formula (I), (II) or (III) may contain one or more asymmetric carbon atoms and can be prepared in form of pure isomers (preferred) or mixtures of isomers such as mixtures of enantiomers like racemates, mixtures of diastereomers, or mixtures of enantiomers and diasteromers such as diastereomeric racemates. The present invention encompasses all these forms. Mixtures can be separated in a manner known per se, e.g. by column chromatography, thin layer chromatography (TLC), high performance liquid chromatography (HPLC), or crystallization.

ii) A particular embodiment of the invention relates to thiophene derivatives according to embodiment i), wherein $R^1$ represents an ethyl group.

iii) A particular embodiment of the invention relates to thiophene derivatives according to embodiment i), wherein $R^1$ represents a methyl group.

iv) A particular embodiment of the invention relates to thiophene derivatives according to embodiment i), wherein $R^1$ represents a trifluoromethyl group.

v) Another particular embodiment of the invention relates to thiophene derivatives according to any one of the embodiments i) to iv), wherein $R^2$ represents a methoxy group, and $R^3$ and $R^4$ represent hydrogen.

vi) Another particular embodiment of the invention relates to thiophene derivatives according to any one of the embodiments i) to iv), wherein $R^2$ represents hydrogen, and $R^3$ and $R^4$ represent $C_{1-4}$-alkyl.

vii) Another particular embodiment of the invention relates to thiophene derivatives according to embodiment vi), wherein $R^3$ and $R^4$ represent a methyl group.

viii) Another particular embodiment of the invention relates to thiophene derivatives according to embodiment vi), wherein $R^3$ and $R^4$ represent an ethyl group.

ix) A particularly preferred embodiment of the invention relates to thiophene derivatives according to embodiment vi), wherein $R^3$ represents a methyl group, and $R^4$ represents an ethyl group.

x) Another particular embodiment of the invention relates to thiophene derivatives according to any one of the embodiments i) to iv), wherein $R^2$ represents hydrogen, $R^3$ represents a methoxy group, and $R^4$ represents a chlorine atom.

xi) Another particular embodiment of the invention relates to thiophene derivatives according to any one of the embodiments i) to iv), wherein $R^2$ represents hydrogen, $R^3$ represents a methyl group, and $R^4$ represents a chlorine atom.

xii) Another particular embodiment of the invention relates to thiophene derivatives according to any one of the embodiments i) to xi), wherein $R^5$ and $R^6$ represent hydrogen.

xiii) Another particularly preferred embodiment of the invention relates to thiophene derivatives according to embodiment xii), wherein n represents 0 and m represents 1.

xiv) Another particular embodiment of the invention relates to thiophene derivatives according to embodiment xii), wherein n represents 1 and m represents 1.

xv) Another particular embodiment of the invention relates to thiophene derivatives according to any one of the embodiments i) to xi), wherein m represents 1, and $R^5$ and $R^6$ represent hydroxy.

xvi) Another particular embodiment of the invention relates to thiophene derivatives according to embodiment xv), wherein n represents 0.

xvii) Another particular embodiment of the invention relates to thiophene derivatives according to any one of the embodiments i) to xi), wherein $R^5$ represents hydrogen, and $R^6$ represents hydroxy.

xviii) A further special embodiment of the invention relates to thiophene derivatives according to embodiment i), wherein $R^1$ represents trifluoromethyl, methyl or ethyl, $R^2$, $R^5$ and $R^6$ represent hydrogen, $R^3$ and $R^4$ represent $C_{1-4}$-alkyl, n represents 0, and m represents 1.

xix) Specific thiophene compounds according to Formula (I) are:
3-{4-[3-(3-ethyl-5,5-dimethyl-4,5,6,7-tetrahydro-benzo[c]thiophen-1-yl)-3-oxo-propyl]-2,6-dimethyl-phenyl}-propionic acid;
3-{4-[3-(5,5-dimethyl-3-trifluoromethyl-4,5,6,7-tetrahydro-benzo[c]thiophen-1-yl)-3-oxo-propyl]-2-ethyl-6-methyl-phenyl}-propionic acid;
3-{2-ethyl-6-methyl-4-[3-oxo-3-(3,5,5-trimethyl-4,5,6,7-tetrahydro-benzo[c]thiophen-1-yl)-propyl]-phenyl}-propionic acid; and
3-{2-ethyl-4-[3-(3-ethyl-5,5-dimethyl-4,5,6,7-tetrahydro-benzo[c]thiophen-1-yl)-3-oxo-propyl]-6-methyl-phenyl}-propionic acid.

xx) A further specific thiophene compound according to Formula (I) is 3-{2,6-dimethyl-4-[3-oxo-3-(3,5,5-trimethyl-4,5,6,7-tetrahydro-benzo[c]thiophen-1-yl)-propyl]-phenyl}-propionic acid.

xxi) A further aspect of the invention relates to novel thiophenes of Formula (II)

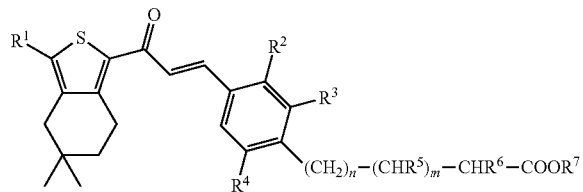

Formula (II)

wherein $R^1$, $R^2$, $R^3$, $R^4$, $R^5$, $R^6$, n and m are as defined for Formula (I) above, and
$R^7$ represents hydrogen, methyl, ethyl, or tert-butyl; and salts as well as solvent complexes of such compounds.

xxii) Yet another aspect of the invention relates to novel thiophenes of Formula (III)

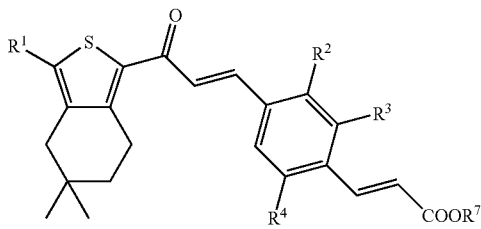

Formula (III)

wherein $R^1$, $R^2$, $R^3$ and $R^4$ are as defined for Formula (I) above, and
$R^7$ represents hydrogen, methyl, ethyl, or tert-butyl; and salts as well as solvent complexes of such compounds.

The compounds of Formula (I) and their pharmaceutically acceptable salts can be used as medicaments, e.g. in the form of pharmaceutical compositions for enteral, parental or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils.

The production of the pharmaceutical compositions can be effected in a manner which will be familiar to any person skilled in the art (see for example Mark Gibson, Editor, Pharmaceutical Preformulation and Formulation, IHS Health Group, Englewood, Colo., USA, 2001; Remington, The Science and Practice of Pharmacy, 20th Edition, Philadelphia College of Pharmacy and Science) by bringing the described compounds of Formula (I) or their pharmaceutically acceptable salts, optionally in combination with other therapeutically valuable substances, into a galenical administration form together with suitable, non-toxic, inert, pharmaceutically acceptable solid or liquid carrier materials and, if desired, usual pharmaceutical adjuvants.

The pharmaceutical compositions comprising a compound of Formula (I) are useful for the prevention and/or treatment of diseases or disorders associated with an activated immune system.

Such diseases or disorders are selected from the group consisting of rejection of transplanted organs, tissue or cells; graft-versus-host diseases brought about by transplantation; autoimmune syndromes including rheumatoid arthritis; systemic lupus erythematosus; antiphospholipid syndrome; Hashimoto's thyroiditis; lymphocytic thyroiditis; multiple sclerosis; myasthenia gravis; type I diabetes; uveitis; episcleritis; scleritis; Kawasaki's disease, uveo-retinitis; posterior uveitis; uveitis associated with Behcet's disease; uveo-meningitis syndrome; allergic encephalomyelitis; chronic allograft vasculopathy; post-infectious autoimmune diseases including rheumatic fever and post-infectious glomerulonephritis; inflammatory and hyperproliferative skin diseases; psoriasis; psoriatic arthritis; atopic dermatitis; myopathy; myositis; osteomyelitis; contact dermatitis; eczematous dermatitis; seborrhoeic dermatitis; lichen planus; pemphigus; bullous pemphigoid; epidermolysis bullosa; urticaria; angioedema; vasculitis; erythema; cutaneous eosinophilia; acne; scleroderma; alopecia greata; keratoconjunctivitis; vernal conjunctivitis; keratitis; herpetic keratitis; dystrophia epithelialis corneae; corneal leukoma; ocular pemphigus; Mooren's ulcer; ulcerative keratitis; scleritis; Graves' opthalmopathy; Vogt-Koyanagi-Harada syndrome; sarcoidosis; pollen allergies; reversible obstructive airway disease; bronchial asthma; allergic asthma; intrinsic asthma; extrinsic asthma; dust asthma; chronic or inveterate asthma; late asthma and airway hyper-responsiveness; bronchiolitis; bronchitis; endometriosis; orchitis; gastric ulcers; ischemic bowel diseases; inflammatory bowel diseases; necrotizing enterocolitis; intestinal lesions associated with thermal burns; coeliac disease; proctitis; eosinophilic gastroenteritis; mastocytosis; Crohn's disease; ulcerative colitis; vascular damage caused by ischemic diseases and thrombosis; atherosclerosis; fatty heart; myocarditis; cardiac infarction; aortitis syndrome; cachexia due to viral disease; vascular thrombosis; migraine; rhinitis; eczema; interstitial nephritis; IgA-induced nephropathy; Goodpasture's syndrome; hemolytic-uremic syndrome; diabetic nephropathy; glomerulosclerosis; glomerulonephritis; tubulointerstitial nephritis; interstitial cystitis; multiple myositis; Guillain-Barré syndrome; Meniere's disease; polyneuritis; multiple neuritis; myelitis; mononeuritis; radiculopathy; hyperthyroidism; Basedow's disease; thyrotoxicosis; pure red cell aplasia; aplastic anemia; hypoplastic anemia; idiopathic thrombocytopenic purpura; autoimmune hemolytic anemia; autoimmune thrombocytopenia; agranulocytosis; pernicious anemia; megaloblastic anemia; aneryth-roplasia; osteoporosis; fibroid lung; idiopathic interstitial pneumonia; dermatomyositis; leukoderma vulgaris; ichthyosis vulgaris; photoallergic sensitivity; cutaneous T cell lymphoma; polyarteritis nodosa; Huntington's chorea; Sydenham's chorea; myocardosis; myocarditis; scleroderma; Wegener's granuloma; Sjogren's syndrome; adiposis; eosinophilic fascitis; lesions of gingiva, periodontium, alveolar bone, substantia ossea dentis; male pattern alopecia or alopecia senilis; muscular dystrophy; pyoderma; Sezary's syndrome; hypophysitis; chronic adrenal insufficiency; Addison's disease; ischemia-reperfusion injury of organs which occurs upon preservation; endotoxin shock; pseudomembranous colitis; colitis caused by drug or radiation; ischemic acute renal insufficiency; chronic renal insufficiency; lung cancer; malignancy of lymphoid origin; acute or chronic lymphocytic leukemias; lymphoma; pulmonary emphysema; cataracta; siderosis; retinitis pigmentosa; senile macular degeneration; vitreal scarring; corneal alkali burn; dermatitis erythema; ballous dermatitis; cement dermatitis; gingivitis; periodontitis; sepsis; pancreatitis; peripheral artery disease; carcinogenesis; solid cancer tumors; metastasis of carcinoma; hypobaropathy; autoimmune hepatitis; primary biliary cirrhosis; sclerosing cholangitis; partial liver resection; acute liver necrosis; cirrhosis; alcoholic cirrhosis; hepatic failure; fulminant hepatic failure; late-onset hepatic failure; and "acute-on-chronic" liver failure.

Preferred diseases or disorders to be treated and/or prevented with the compounds of Formula (I) are selected from the group consisting of rejection of transplanted organs such as kidney, liver, heart, lung, pancreas, cornea, and skin; graft-versus-host diseases brought about by stem cell transplantation; autoimmune syndromes including rheumatoid arthritis, multiple sclerosis, inflammatory bowel diseases such as Crohn's disease and ulcerative colitis, psoriasis, psoriatic arthritis, thyroiditis such as Hashimoto's thyroiditis, uvec-retinitis; atopic diseases such as rhinitis, conjunctivitis, dermatitis; asthma; type I diabetes; post-infectious autoimmune diseases including rheumatic fever and post-infectious glomerulonephritis; solid cancers and tumor metastasis.

Particularly preferred diseases or disorders to be treated and/or prevented with the compounds of Formula (I) are selected from the group consisting of rejection of transplanted organs selected from kidney, liver, heart and lung; graft-versus-host diseases brought about by stem cell transplantation; autoimmune syndromes selected from rheumatoid arthritis, multiple sclerosis, psoriasis, psoriatic arthritis, Crohn's disease, and Hashimoto's thyroiditis; and atopic dermatitis.

The present invention also relates to a method for the prevention or treatment of a disease or disorder mentioned herein comprising administering to a subject a pharmaceutically active amount of a compound of Formula (I).

Furthermore, compounds of the Formula (I) are also useful, in combination with one or several immunomodulating agents, for the prevention and/or treatment of the diseases and disorders mentioned herein. According to a preferred embodiment of the invention, said agents are selected from the group consisting of immunosuppressants, corticosteroids, NSAID's, cytotoxic drugs, adhesion molecule inhibitors, cytokines, cytokine inhibitors, cytokine receptor antagonists and recombinant cytokine receptors.

The present invention also relates to the use of a compound of Formula (I) for the preparation of a pharmaceutical composition, optionally for use in combination with one or several immunomodulating agents, for the prevention or treatment of the diseases and disorders mentioned herein.

The present invention also relates to pro-drugs of a compound of Formula (I) that convert in vivo to the compound of Formula (I) as such. Any reference to a compound of Formula (I) is therefore to be understood as referring also to the corresponding pro-drugs of the compound of Formula (I), as appropriate and expedient.

The compounds of Formula (I) can be manufactured by the methods given below, by the methods given in the Examples or by analogous methods. Optimum reaction conditions may vary with the particular reactants or solvents used, but such conditions can be determined by a person skilled in the art by routine optimisation procedures.

Compounds of the Formula (I) of the present invention can be prepared according to the general sequence of reactions outlined below. Only a few of the synthetic possibilities leading to compounds of Formula (I) are described.

Structure 1

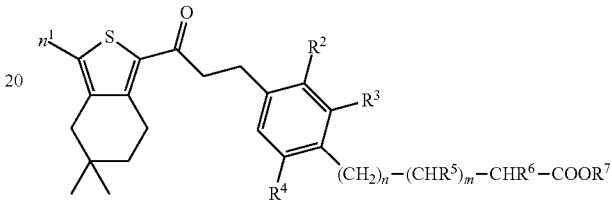

The compounds of Formula (I) may be prepared by reacting a compound of Structure 1 with a base such as aq. LiOH, aq. NaOH, aq. KOH, etc. or an acid such as aq. HCl, TFA, etc. in the presence or absence of additional solvents such as THF, dioxane, DMF, DMSO, DCM etc. Compounds of Structure 1 may be prepared by hydrogenation of a compound of Formula (II), or in case n represents 0, m represents 1 and $R^5$ and $R^6$ represent hydrogen, by hydrogenation of a compound of Formula (III) in the presence of a catalyst such as Pd/C, Pt/C etc. in a solvent such as methanol, ethanol, THF etc., or mixtures thereof.

Structure 2

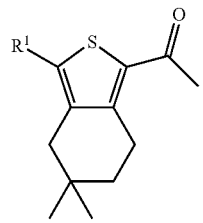

Structure 3

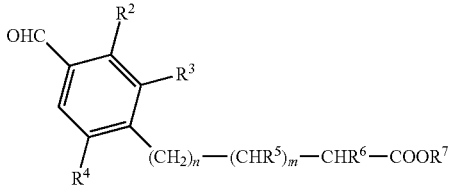

Structure 4

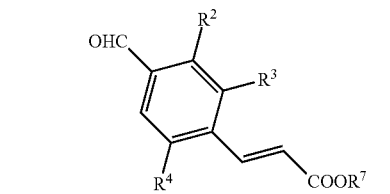

Compounds of Formula (II) may be prepared by condensing a compound of Structure 2 with a compound of Structure 3 in the presence of HCl in a solvent such as ethanol, isopropanol, etc., or mixtures thereof, or in the presence of NaOH, LiOH, or KOH in a solvent such as methanol, ethanol, isopropanol, or mixtures thereof, at temperatures preferably between 0° C. and 70° C. Similarly, a compound of Formula (III) may be prepared by condensing a compound of Structure 2 with a compound of Structure 4.

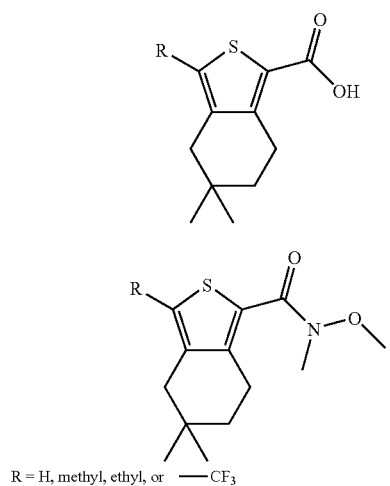

R = H, methyl, ethyl, or ⎯CF₃

A compound of Structure 2 may be prepared by reacting a compound of Structure 5, wherein R is methyl, ethyl or trifluoromethyl, with MeLi in a solvent such as diethyl ether, or THF or mixtures thereof at temperatures between −20° C. and 35° C. Alternatively, a compound of Structure 2 may also be prepared by reacting a compound of Structure 6, wherein R is methyl, ethyl or trifluoromethyl, with methyl magnesiumbromide, methyl magnesiumchloride, or methyl magnesiumiodide. The Weinreb amide of Structure 6 may be prepared by reacting an acid of Structure 5 with N,O-dimethylhydroxylamine hydrochloride in the presence of a coupling reagent such as EDC, DCC, etc. (Lit. e.g. M. Mentzel, H. M. R. Hoffmann, *Journal fuer Praktische Chemie/Chemiker-Zeitung* 339 (1997), 517-524; J. Singh, N. Satyamurthi, I. S. Aidhen, *Journal fuer Praktische Chemie* (Weinheim, Germany) 342 (2000), 340-347; V. K. Khlestkin, D. G. Mazhukin, *Current Organic Chemistry* 7 (2003), 967-993).

The compounds of Structure 5 may be prepared by reacting a compound of Structure 7 with an aq. base such as aq. NaOH, aq. LiOH, aq. KOH, etc. or an acid such as aq. HCl, TFA, etc. in a solvent such as water, ethanol, methanol, THF, etc., or mixtures thereof.

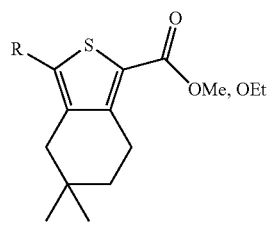

The compounds of Structure 7 are prepared by treating a compound of Structure 8 with a non-aqueous base such as NaOMe, NaOEt, KO-tert-Bu, DBU, etc. in a solvent such as methanol, ethanol, THF, DMF, etc., or mixtures thereof, preferably at elevated temperatures.

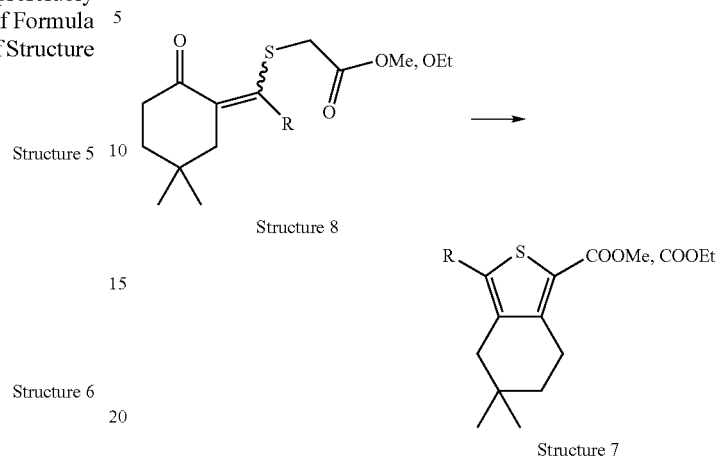

The compounds of Structure 8 are prepared by treating a compound of Structure 9 with a 2-mercaptoacetic acid ester in the presence of a base such a NaH, NaOEt, NaOMe, K-tert-butoxide, etc. in THF, dioxane, DMF, ethanol, methanol, etc., or mixtures thereof. In addition, the compounds of Structure 5 may also be prepared in a one-pot-three-step procedure starting from a compound of Structure 9 following the above reaction sequence.

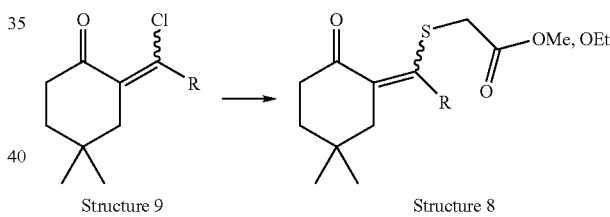

The compounds of Structure 9 are prepared by reacting a compound of Structure 10 with a chlorinating agent such as oxalylchloride in a solvent such as DCM, CHCl₃, THF, etc. (Lit. e.g. R. E. Mewshaw, Richard E. *Tetrahedron Lett.* 30 (1989), 3753-3756; F. A. Lakhvich, T. S. Khlebnikova, A. A. Akhrem, *Zhurnal Organicheskoi Khimii* 25 (1989), 2541-2549).

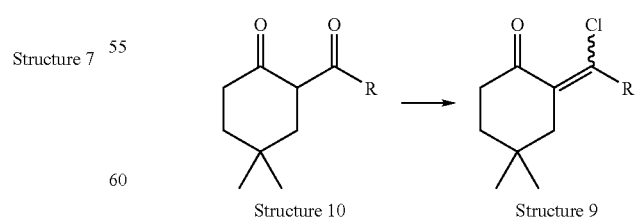

The compounds of Structure 10, wherein R represents hydrogen, methyl or ethyl, may be prepared by acylating the compound of Structure 11 with an appropriate acylating agent such as ethyl or methyl formate, methyl or ethyl acetate, methyl or ethyl propionate, chloroformate, acetyl chloride, etc. in the presence of a base such as K-tert-butylate, NaOMe, NaH, LDA, etc. in a solvent such as THF, toluene, EtOH etc. at temperatures between 0 and 60° C. (Lit. e.g. Ch. Kashima, S. Shibata, H. Yokoyama, T. Nishio, *Journal of Heterocyclic Chemistry* 40 (2003), 773-782; I. Yavari, Issa; M. Bayat, *Tetrahedron* 59 (2003), 2001-2005; J. P. Konopelski, J. Lin, P. J. Wenzel, H. Deng, G. I. Elliott, B. S. Gerstenberger, *Organic Letters* 4 (2002), 4121-4124; C. Wiles, P. Watts, S. J. Haswell, E. Pombo-Villar, *Tetrahedron Letters* 43 (2002), 2945-2948; R. Faure, A. Frideling, J.-P. Galy, I. Alkorta, J. Elguero, *Heterocycles* 57 (2002), 307-316; via imine: M. Hammadi, D. Villemin, *Synthetic Communications* 26 (1996), 2901-2904).

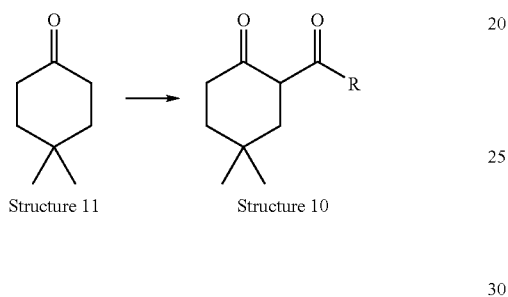

Structure 11          Structure 10

The compound of Structure 11 is prepared according to procedures known to a person skilled in the art (Lit. e.g. M. E. Flaugh, T. A. Crowell, D. S. Farlow, *Journal of Organic Chemistry* 45 (1980), 5399-5400; A. M. Badger, M. J. Dimartino, C. K. Mirabelli, E. N. Cheeseman, J. W. Dorman, D. H. Picker, D. A. Schwartz, Eur. Pat. Appl. EP 310321 A2 (1989); N. R. Natale, R. O. Hutchins, *Organic Preparations and Procedures International* 9 (1977), 103-108; L. M. Rice, B. S. Sheth, J. W. Wheeler, *Journal of Heterocyclic Chemistry* 10 (1973), 731-735).

In addition, the compounds of Structure 5, wherein R represents a methyl or ethyl group, are preferably prepared from a compound of Structure 5 wherein R represents hydrogen (Structure 12) by reacting the latter compound with an excess of a strong base such as n-BuLi, tert-BuLi, LDA, etc. in a solvent such as THF, diethyl ether, etc. followed by the appropriate alkylating agent (e.g. methyliodide, ethyliodide, Lit. e.g. W.-D. Liu, C.-C. Chi, I.-F. Pai, A.-T. Wu, W.-S. Chung, *Journal of Organic Chemistry* 67 (2002), 9267-9275; D. W. Knight, A. P. Nott, *Tetrahedron Letters* 21 (1980), 5051-5054; R. Raap, *Canadian Journal of Chemistry* 49 (1971), 2155-2157).

The compounds of Structure 2 wherein $R^1$ represents a trifluoromethyl group are preferably prepared by the sequence outlined below. Hence, the compound of Structure 12 is transformed into its Weinreb amide of Structure 13, which is iodinated upon treatment with a strong base such as LDA followed by the addition of iodine in a solvent such as THF at low temperature (e.g. −78° C.). The iodinated compound of Structure 14 is reacted with methyl chlorodifluoroacetate as described in the literature (e.g. D. E. Nichols, S. Frescas, D. Marona-Lewicka, X. Huang, B. L. Roth, G. A. Gudelksy, J. F. Nash, *J. Med. Chem.* 37 (1994), 4346-4351) to give the trifluoromethyl compound of Structure 15. Treatment of the compound Structure 15 with a methyl Grignard reagent or methyl lithium furnishes the compound of Structure 2 wherein $R^1$ represents a trifluoromethyl group.

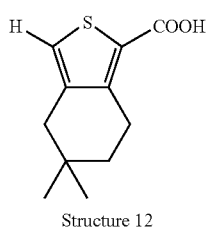

Structure 12

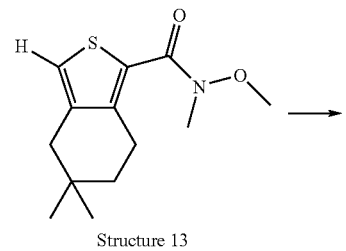

Structure 13

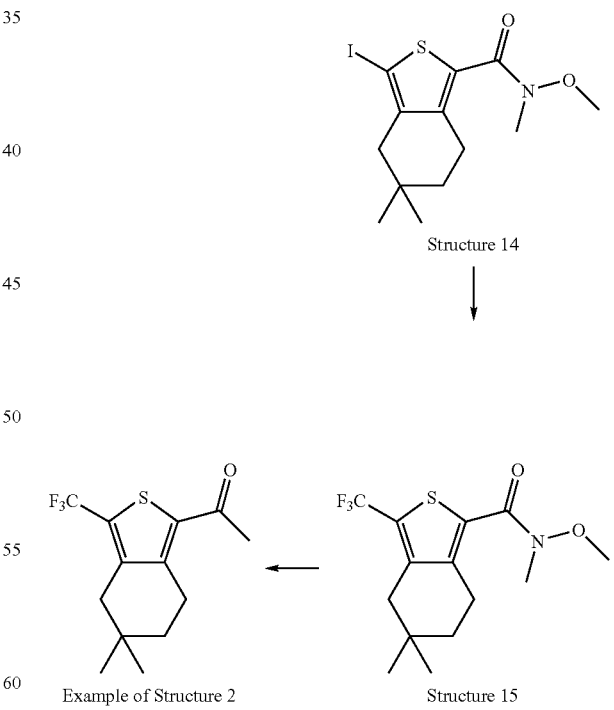

Structure 14

Example of Structure 2          Structure 15

The following schemes illustrate synthetic routes to prepare compounds of Structure 3 and 4.

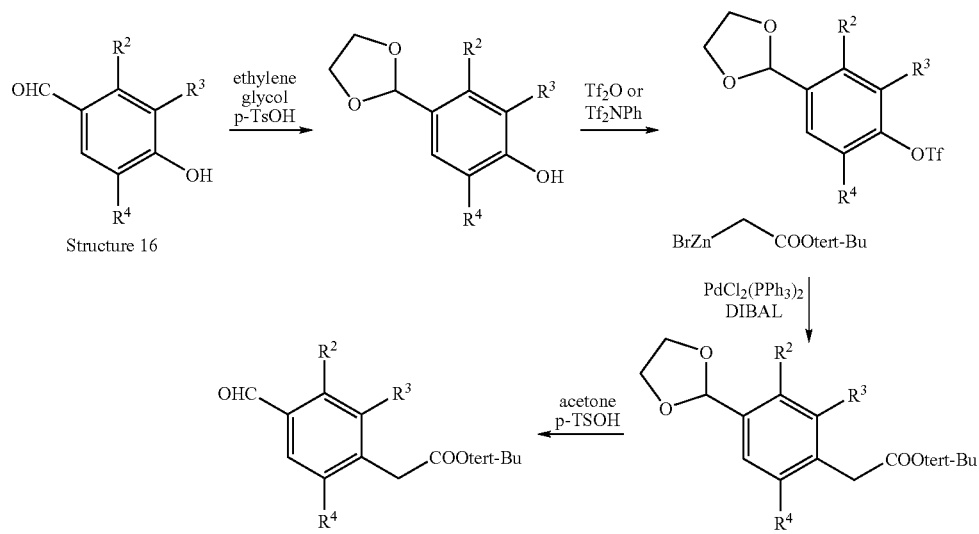
(Lit. e.g. F. Orsini, F. Pelizzoni, *Synthetic Comm.* 17 (1987), 1389-1402)
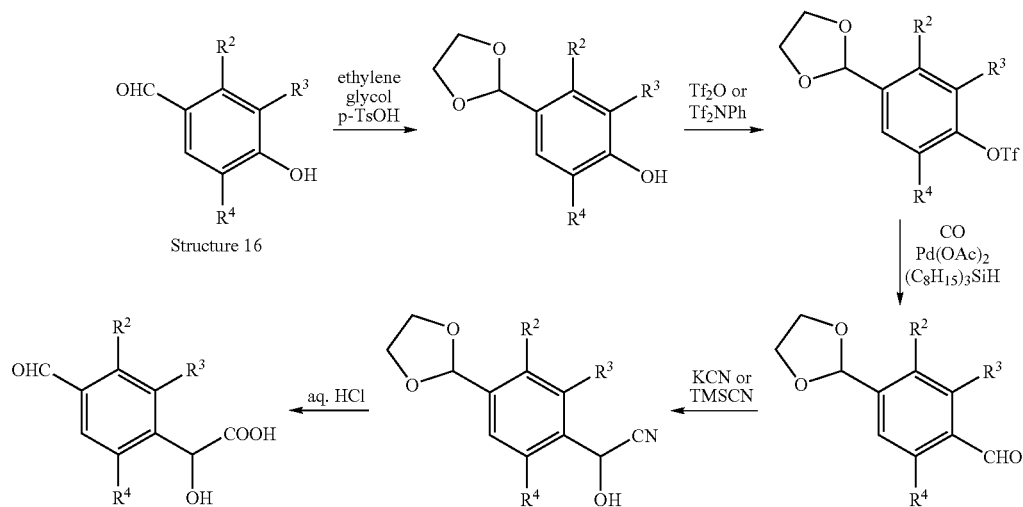
(Lit. e.g. H. Kotsuki, P. K. Datta, H. Suenaga, *Synthesis* 1996, 470-472; for bromide or iodide instead of triflate see e.g. V. P. Baillargeon, J. K. Stille, *J. Am. Chem. Soc.* 108 (1986), 452-461; M. J. Gomez-Escalonilla, F. Langa, J.-M. Rueff, L. Oswald, J. F. Nierengarten, *Tetrahedron Lett.* 43 (2002), 7507-7511; H. Aust, D. Ickenroth, H. Meier, *J. Prakt Chem.* 341 (1999), 523-528; Y. Li, B. He, B. Qin, X. Feng, G, Zhang, *J. Org. Chem.* 69 (2004), 7910-7913).
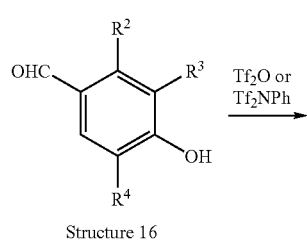
-continued
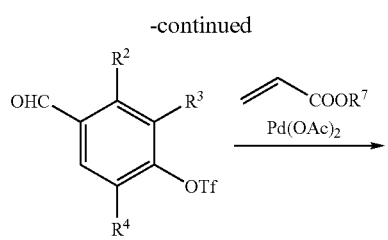
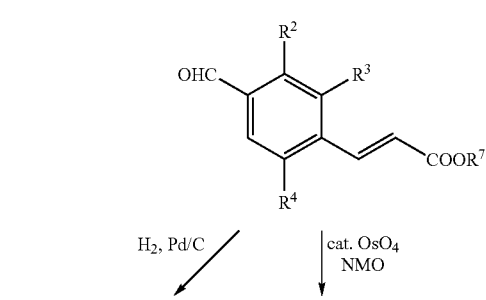

15
-continued
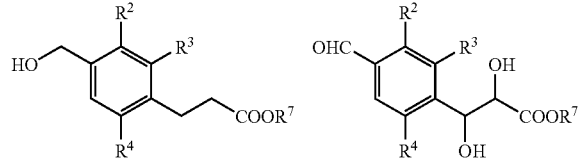
16
-continued
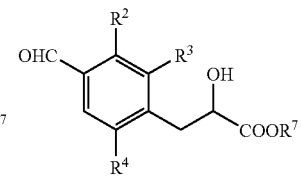
(Lit. e.g. G. Battistuzzi, S. Cacchi, G. Fabrizi, *Org. Lett.* 5 (2003), 777-780; N.J. Lawrence, S. Brown, *Tetrahedron* 58 (2002), 613-619; D. J. Wardrop, M. S. Burge, *Chem. Comm.* 2004, 1230-1231)
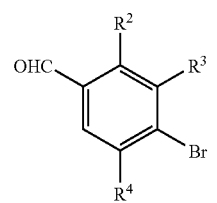 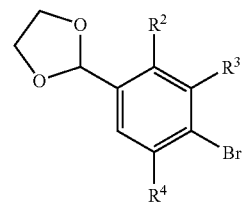 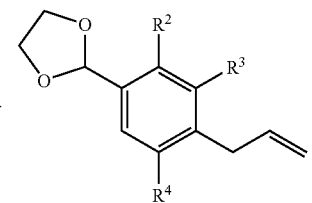
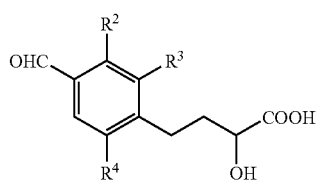 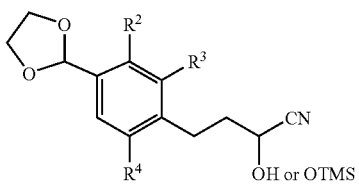 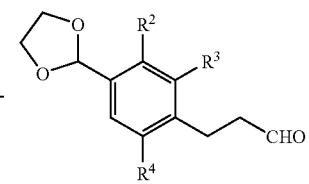
(Lit. e.g. Y. Li, B. He, B. Qin, X. Feng, G, Zhang, *J. Org. Chem.* 69 (2004), 7910-7913; T. Azemi, M. Kitamura, K. Narasaka, *Tetrahedron* 60 (2004), 1339-1344; A. Krasovskiy, P. Knochel, *Angew. Chem. Int. Ed.* 43 (2004), 3333-3336; T. P. Zabawa, D. Kasi, S. R. Chemler, *J. Am. Chem. Soc.* 127 (2005), 11250-11251).
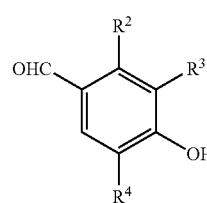 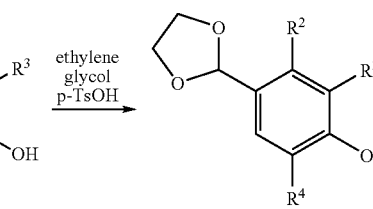 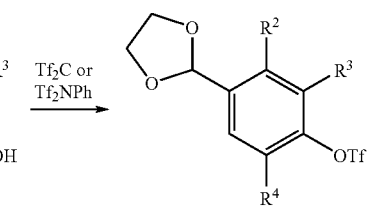
Structure 16
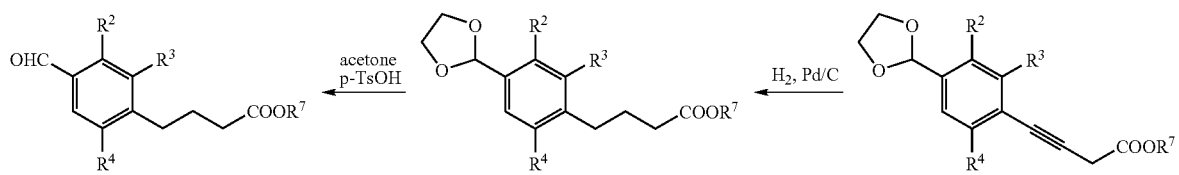

(Lit. e.g. W. P. Gallagher, R. E. Maleczka, *J. Org. Chem.* 68 (2003), 6775-6779, A.-Y. Peng, Y.-X. Ding, *J. Am. Chem. Soc.* 125 (2003), 15006-15007).

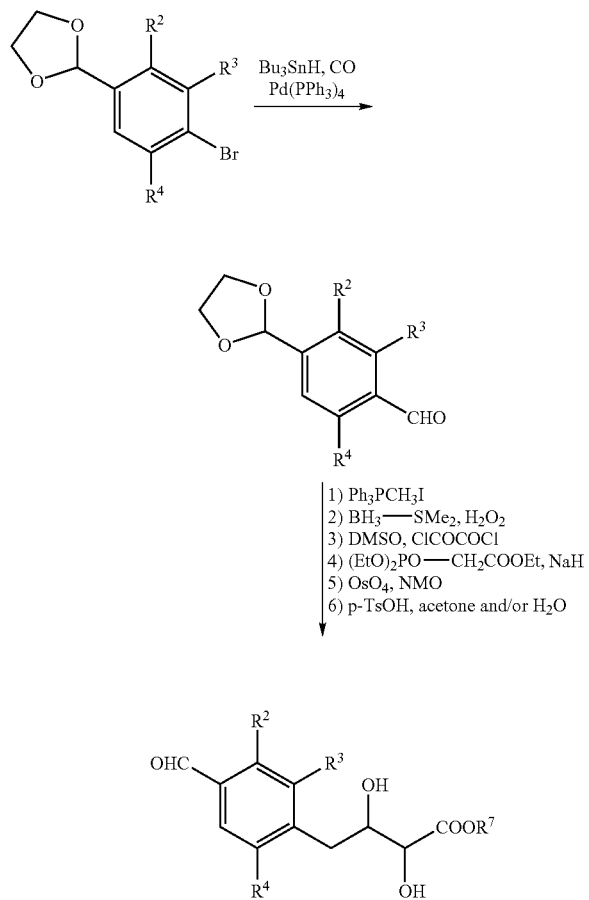

(Lit. e.g. R. A. Fernandes, M. S. Bodas, P. Kumar, *Tetrahedron* 58 (2002), 1223-1227; V. P. Baillargeon, J. K. Stille, *J. Am. Chem. Soc.* 108 (1986), 452-461).

An alternative route to prepare compounds of Structure 1 is given in the scheme below. The compounds of Structure 17 are obtained by condensing a compound of Structure 2 with a compound of Structure 16 under the either basic or acidic conditions mentioned above. The compounds of Structure 16 are either commercially available or are prepared following standard methodology known to a person skilled in the art. Treatment of a compound of Structure 17 with e.g. trifluoromethanesulfonic anhydride in the presence of a base such as triethylamine or pyridine affords the compounds of Structure 18. Pd-catalysed Heck-type coupling reaction of a compound of Structure 18 with a compound of Structure 19 gives the corresponding compound of Structure 20 (Lit. e.g. G. Battistuzzi, S. Cacchi, G. Fabrizi, *Org. Lett* 5 (2003), 777-780). Depending on the reaction conditions applied, the alcohol functionality present in the case where $R^6$ represents a hydroxy group may require temporary protection. The double bond present in the compound of Structure 20 may then be further elaborated to the desired motif disclosed in Structure 1. These steps are in analogy to those outlined for the preparation of compounds of Structure 3 and 4 above and thus may include simple hydrogenation to obtain the saturated derivative or dihydroxylation using e.g. $KMnO_4$ or a catalytic amount of $OsO_4$ in the presence of N-methyl morpholine-N-oxide (NMO) whereupon the reductive removal of the benzylic alcohol may follow (Lit. e.g. N.J. Lawrence, S. Brown, *Tetrahedron* 58 (2002), 613-619; D. J. Wardrop, M. S. Burge, *Chem. Comm.* 2004, 1230-1231). The cross coupling reaction may also be carried out with an alkyne rather than an alkene (Sonogashira coupling, e.g. W. P. Gallagher, R. E. Maleczka, *J. Org. Chem.* 68 (2003), 6775-6779; A.-Y. Peng, Y.-X. Ding, *J. Am. Chem. Soc.* 125 (2003), 15006-15007). The such produced phenylacetylene derivative may then be hydrogenated in a sequencial or a one-step fashion to the corresponding saturated compound.

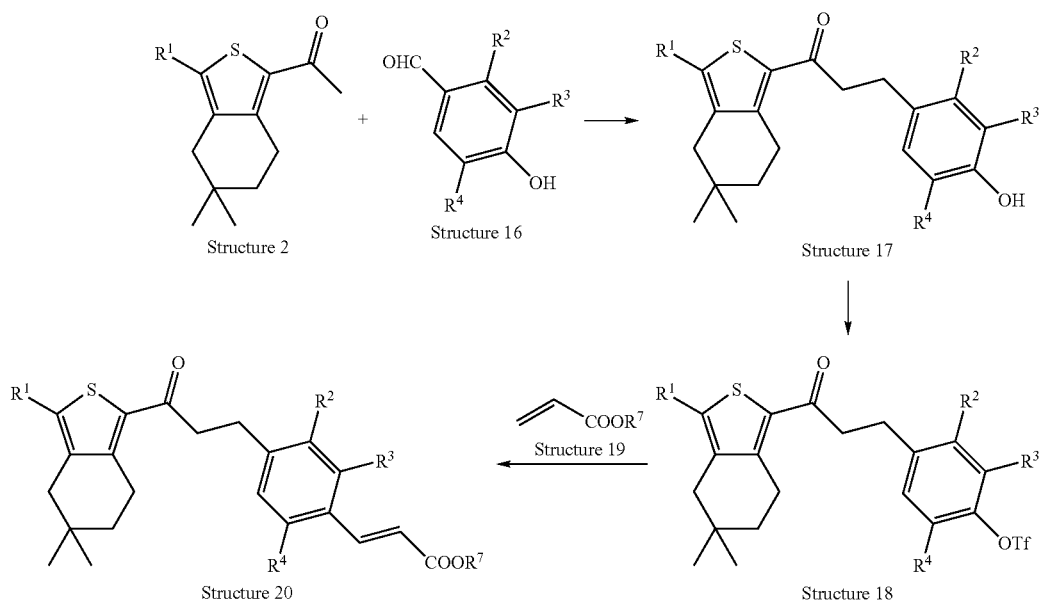

EXAMPLES

The following examples illustrate the invention but do not at all limit the scope thereof.

All temperatures are stated in ° C. Compounds are characterized by $^{1}$H-NMR (300 MHz) or $^{13}$C-NMR (75 MHz) (Varian Oxford; chemical shifts are given in ppm relative to the solvent used; multiplicities: s=singlet, d=doublet, t=triplet, p=pentuplet, hex=hexet, hept=heptet, m=multiplet, br=broad, coupling constants are given in Hz); by LC-MS (Finnigan Navigator with HP 1100 Binary Pump and DAD, column: 4.6×50 mm, Zorbax SB-AQ, 5 µm, 120 Å, gradient: 5-95% acetonitrile in water, 1 min, with 0.04% trifluoroacetic acid, flow: 4.5 mL/min), $t_R$ is given in min; by TLC (TLC-plates from Merck, Silica gel 60 $F_{254}$); or by melting point. Compounds are purified by preparative HPLC (conditions if not stated otherwise: column: X-terra RP18, 50×19 mm, 5 µm, gradient: 10-95% acetonitrile in water containing 0.5% of formic acid) or by MPLC (Labomatic MD-80-100 pump, Linear UVIS-201 detector, column: 350×18 mm, Labogel-RP-18-5s-100, gradient: 10% methanol in water to 100% methanol).

Abbreviations (as Used Herein):
aq. aqueous
atm atmosphere
BSA bovine serum albumin
Bu butyl
cat. catalytic
CC column chromatography
d day(s)
DBU 1,8-diazabicylo[5.4.0]undec-7-en
DCC dicyclohexyl carbodiimide
DCM dichloromethane
DIBAL diisobutylaluminium hydride
DIPEA diisopropyl-ethylamine, Hünig's base, ethyl-diisopropylamine
DMF dimethylformamide
DMSO dimethylsulfoxide
EA ethyl acetate
EDC N-(3-dimethylaminopropyl)-N'-ethyl-carbodiimide
Et ethyl
h hour(s)
HPLC high performance liquid chromatography
HV high vacuum conditions
i-Prop isopropyl
LC-MS liquid chromatography-mass spectrometry
LDA lithium diisopropyl amide
Me methyl
min minute(s)
MPLC medium pressure liquid chromatography
NMO N-methyl morpholine-N-oxide
NMP 1-methyl-2-pyrrolidone
OAc acetate
OTMS trimethylsilyloxy
Ph phenyl
prep. preparative
p-TSOH para-toluenesulfonic acid
rt room temperature
sat. saturated
sip sphingosine 1-phosphate
TBTU 2-(1H-benzotriazole-1-yl)-1,2,3,3-tetramethyluronium tetrafluoroborate
Tf trifluoromethane sulfonyl
TFA trifluoroacetic acid
THF tetrahydrofuran
TLC thin layer chromatography
TMSCN trimethylsilyl cyanide
$t_R$ retention time Scaffold A

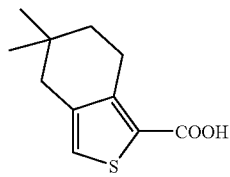

a) To a solution of 4,4-dimethyl-cyclohex-2-enone (50 g, 403 mmol) in EA (230 mL) a suspension of Pd/C (2.5 g, 10% Pd) in EA is added. The suspension is stirred at rt for 2 h under 1 bar $H_2$. The catalyst is filtered off and the solvent of the filtrate is carefully evaporated to give 4,4-dimethyl-cyclohexanone (50 g) as a colourless oil which slowly crystallizes; $^{1}$H NMR (CDCl$_3$): δ 2.34 (t, J=6.4 Hz, 4H), 1.66 (t, J=6.4 Hz, 4H), 1.09 (s, 6H).

b) To an ice-cold solution of K-tert-butylate (24.5 g, 109 mmol, 50% solution in tert-butanol) in THF (700 mL), ethylformate (120 mL, 123 mmol) is slowly added. The mixture is stirred at rt for 30 min before a solution of 4,4-dimethyl-cyclohexanone (50 g, 396 mmol) in ethylformate (50 mL) and THF (70 mL) is added over a period of 20 min. Upon complete addition, stirring is continued at 15-20° C. for 30 min. The orange suspension is poured onto a 10% aq. citric acid solution (200 mL) and brine (200 mL) and extracted with EA (2×200 mL). The organic extracts are washed with 0.2 N aq. NaOH and brine, dried over Na$_2$SO$_4$ and evaporated to dryness to give 5,5-dimethyl-2-oxo-cyclohexanecarbaldehyde (52 g) as a yellow oil; LC-MS: $t_R$=0.89 min, [M+1+CH$_3$CN]+=196.15.

c) To a solution of 5,5-dimethyl-2-oxo-cyclohexanecarbaldehyde (51 g, 331 mmol) in chloroform (250 mL), oxalyl chloride (40 mL, 465 mmol) is rapidly added. After stirring for 3-4 min, ice followed by 2 N aq. NaOH (100 mL) is added. The organic phase is separated and the aq. phase is extracted once more with chloroform. The combined organic extracts are washed with water and dried over Na$_2$SO$_4$. The solvent is removed in vacuo to give 2-chloromethylene-4,4-dimethyl-cyclohexanone (50 g) as a brown oil; LC-MS: $t_R$=0.96 min.

d) To a part (300 mL) of a freshly prepared solution of sodium (21 g, 875 mmol) in ethanol (500 mL), mercaptoacetic acid ethyl ester (50 mL) is added. The resulting solution is added over a period of 10 min to a solution of 2-chloromethylene-4,4-dimethyl-cyclohexanone (50 g, 290 mmol) in THF (170 mL). The mixture becomes warm (50° C.). Upon complete addition, the remaining part of the freshly prepared solution of sodium in ethanol (200 mL) is added to the reaction mixture. The mixture is stirred at rt for 15 min before 1 N aq. LiOH solution (300 mL) is added. The solution is refluxed for 3 h, then stirred at rt for 16 h. The THF and ethanol are removed under reduced pressure and the remaining dark solution is extracted with heptane/EA 3:1 (2×200 mL). The aq. phase is acidified by adding citric acid (30 g) and 2 N aq. HCl (200 mL) and then extracted three times with EA. The combined organic extracts are washed three times with sat. aq. NaHCO$_3$ solution, dried over Na$_2$SO$_4$ and evaporated. The resulting dark brown oil is dissolved in acetonitrile at 60° C. and crystallised at 5° C. The crystals are collected, washed with acetonitrile and dried to give 5,5-dimethyl-4,5,6,7-tetrahydro-benzo[c]thiophene-1-carboxylic acid (31 g) as a slightly grey powder; LC-MS: $t_R$=0.95 min, [M+1+CH$_3$CN]+=252.18; $^1$H NMR (CDCl$_3$): δ 7.15 (s, 1H), 3.05 (t, J=7.0 Hz, 2H), 2.47 (s, 2H), 1.58 (t, J=7.0 Hz, 2H), 0.97 (s, 6H).

Scaffold B

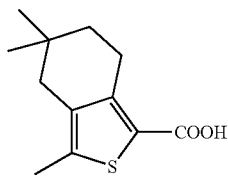

1) Via Scaffold A

At −78° C. a solution of 5,5-dimethyl-4,5,6,7-tetrahydro-benzo[c]thiophene-1-carboxylic acid (5 g, 23.8 mmol) in THF is treated with tert-butyllithium (41 mL, 1.5 M in pentane). The mixture is stirred at −78° C. for 15 min before methyliodide (17.1 g, 120 mmol) is added dropwise. Stirring is continued at −78° C. for 30 min. The mixture is warmed to rt, diluted with water (400 mL), acidified with 10% aq. citric acid solution and extracted three times with EA. The combined organic extracts are dried over MgSO$_4$ and evaporated. The remaining solid is suspended in heptane/diethyl ether, filtered and dried under HV to give 3,5,5-trimethyl-4,5,6,7-tetrahydro-benzo[c]thiophene-1-carboxylic acid (4.01 g) as a beige powder; LC-MS: $t_R$=0.97 min; [M+1]=225.13; $^1$H NMR (D$_6$-DMSO): δ 12.49 (s br, 1H), 2.87 (t, J=6.7 Hz, 2H), 2.26 (s, 5H), 1.45 (t, J=6.7 Hz, 2H), 0.91 (s, 6H).

2) Direct Route Starting from 4,4-dimethyl-cyclohexanone a) To a suspension of NaH (2.88 g, 60% dispersion in mineral oil, 60 mmol) in toluene (25 mL), EA (6.5 mL, 66 mmol) is added. The mixture is stirred at rt for 5 min before a solution of 4,4-dimethyl-cyclohexanone (2.52 g, 20 mmol) in EA (6 mL) is added. The mixture is heated to 55° C. where a vigorous reaction starts. The white to grey suspension turns orange and becomes clear. The clear solution is poured onto ice/water and is extracted with EA. The aq. phase is acidified to pH 4-5 and extracted once more with EA. The combined organic extracts are dried over Na$_2$SO$_4$ and the solvent is removed in vacuo to give 2-acetyl-4,4-dimethyl-cyclohexanone (2.00 g) as a yellow oil; $^1$H NMR (CDCl$_3$): δ 2.35 (t, J=7.0 Hz, 2H), 2.12 (s, 2H), 2.10 (s, 1H), 1.48 (t, J=7.0 Hz, 2H), 0.98 (s, 6H).

b) At 0° C., a solution of 2-acetyl-4,4-dimethyl-cyclohexanone (5.00 g, 29.7 mmol) in chloroform (15 mL) is treated with oxalyl chloride (7.54 g, 59.4 mmol). The mixture is heated to 60° C. and stirred for 15 min before it is poured onto water. The organic phase is separated, washed with sat. aq. NaHCO$_3$ solution and brine, dried over MgSO$_4$ and evaporated to dryness to give crude 2-(1-chloro-ethylidene)-4,4-dimethyl-cyclohexanone (3.2 g, containing regio-isomer) as a brown oil, LC-MS: $t_R$=1.00 min.

c) To a mixture of NaOEt (10 mL of a 2.5 M solution in ethanol, 25 mmol) in THF (10 mL), mercaptoacetic acid ethyl ester (3.09 g, 25.7 mmol) followed by a solution of the above 2-(1-chloro-ethylidene)-4,4-dimethyl-cyclohexanone (3.2 g, 17.14 mmol) is added. The resulting solution is stirred at 60° C. for 45 min. The mixture is diluted with water and extracted with EA. The organic extract is dried over Na$_2$SO$_4$, evaporated and purified by CC on silica gel eluting with heptane/toluene and then heptane/EA to give 3,5,5-trimethyl-4,5,6,7-tetrahydro-benzo[b]thiophene-2-carboxylic acid ethyl ester (3.1 g) as a brown oil containing the regio isomer 3,5,5-trimethyl-4,5,6,7-tetrahydro-benzo[b]thiophene-2-carboxylic acid ethyl ester. An analytical sample is purified by prep. HPLC to give pure 3,5,5-trimethyl-4,5,6,7-tetrahydro-benzo[b]thiophene-2-carboxylic acid ethyl ester as a colourless oil; LC-MS: $t_R$=1.13 min; [M+1]=252.99; $^1$H NMR (CDCl$_3$): δ 4.29 (q, J=7.0 Hz, 2H), 3.00 (t, J=6.4 Hz, 2H), 2.30 (s, 3H), 2.26 (s, 2H), 1.52 (t, J=6.4 Hz, 2H), 1.34 (t, J=7.0 Hz, 3H), 0.96 (s, 6H).

d) To a solution of 3,5,5-trimethyl-4,5,6,7-tetrahydro-benzo[b]thiophene-2-carboxylic acid ethyl ester (3.0 g, 11.9 mmol) in ethanol (100 mL), aq. 2 N LiOH (50 mL) is added. The reaction mixture is stirred at 65° C. for 2 h before the ethanol is removed on a rotavapor. The remaining solution is extracted once with heptane, acidified with citric acid to pH 2 and extracte three times with EA. The EA extracts are combined, dried over Na$_2$SO$_4$, filtered, evaporated and dried to give 3,5,5-trimethyl-4,5,6,7-tetrahydro-benzo[b]thiophene-2-carboxylic acid (1.6 g) as a beige solid containing the regio isomer 3,5,5-trimethyl-4,5,6,7-tetrahydro-benzo[b]thiophene-2-carboxylic acid. LC-MS: $t_R$=0.98 min, [M+1]=225.14.

Scaffold C

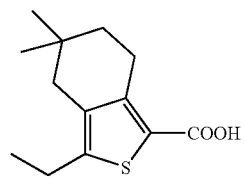

To a cooled solution (−78° C.) of 5,5-dimethyl-4,5,6,7-tetrahydro-benzo[c]thiophene-1-carboxylic acid (960 mg, 4.57 mmol) in THF (19 mL), tert-butyllithium (8 mL, 1.5 M solution in pentane) is added. The mixture is stirred at −78° C. for 10 min before ethyliodide (3.80 g, 24.37 mmol) is added. The reaction mixture is stirred at −78° C. for 3 h. Water/methanol 1:1 (8 mL) followed by 10% aq. citric acid solution is added and the mixture is extracted with EA. The combined organic extracts are washed with brine, dried over Na$_2$SO$_4$ and evaporated. The remaining solid is suspended in acetonitrile (6 mL), heated to 60° C., cooled to rt, filtered and dried to give 3-ethyl-5,5-dimethyl-4,5,6,7-tetrahydro-benzo[c]thiophene-1-carboxylic acid (640 mg) as a slightly beige solid; LC-MS: $t_R$=1.01 min, [M+1+CH$_3$CN]=280.10.

Scaffold D

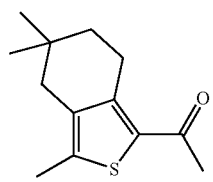

To a suspension of 3,5,5-trimethyl-4,5,6,7-tetrahydro-benzo[c]thiophene-1-carboxylic acid (4.10 g, 18.28 mmol) in diethyl ether (300 mL), methyllithium (23 mL, 1.6 M solution in diethyl ether) is slowly added at rt. The reaction mixture becomes clear, yellow and slightly warm (26° C.), and is stirred for 15 min before it is quenched with water. The organic layer is separated, washed once more with water, dried over MgSO$_4$ and evaporated. The crude product is purified by CC on silica gel eluting with heptane:EA 4:1 to give 1-(3,5,5-trimethyl-4,5,6,7-tetrahydro-benzo[c]thiophen-1-yl)-ethanone (2.80 g) as a pale yellow crystalline solid; LC-MS: t$_R$=1.06 min; [M+1]=223.17; $^1$H NMR (CDCl$_3$): δ 3.00 (t, J=7.0 Hz, 2H), 2.43 (s, 3H), 2.31 (s, 3H), 2.26 (s, 2H), 1.51 (t, J=7.0 Hz, 2H), 0.95 (s, 6H).

Scaffold E

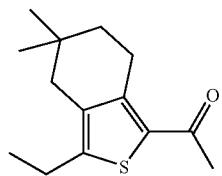

To a solution of 3-ethyl-5,5-dimethyl-4,5,6,7-tetrahydro-benzo[c]thiophene-1-carboxylic acid (2.10 g, 8.81 mmol) in diethyl ether (100 mL), a solution of methyllithium (11 mL, 1.6 M solution in diethyl ether) is added at rt. The pale yellow solution is stirred at rt for 15 min before another portion of methyllithium (2 mL) is added. Stirring is continued for 15 min, a further portion of methyllithium (1 mL) is added, and the mixture is again stirred for 15 min at rt. The reaction is quenched with water. The organic layer is separated, washed once more with water, dried over MgSO$_4$ and evaporated. The crude product is purified by CC on silica gel eluting with heptane:EA 7:3 to give 1-(3-ethyl-5,5-dimethyl-4,5,6,7-tetrahydro-benzo[c]thiophen-1-yl)-ethanone (1.65 g) as a pale yellow solid; LC-MS: t$_R$=1.00 min; [M+1]=237.15; $^1$H NMR (CDCl$_3$): δ 3.03 (t, J=7.0 Hz, 2H), 2.73 (q, J=7.6 Hz, 2H), 2.47 (s, 3H), 2.31 (s, 2H), 1.55 (t, J=7.0 Hz, 2H), 1.28 (t, J=7.6 Hz, 3H), 0.97 (s, 6H).

Scaffold F

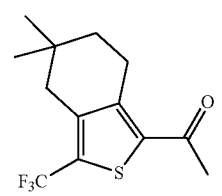

a) To a solution of 5,5-dimethyl-4,5,6,7-tetrahydro-benzo[c]thiophene-1-carboxylic acid (20 g, 95 mmol) in DMSO (150 mL) is added N,O-dimethylhydroxylamine hydrochloride (12.06 g, 124 mmol) and DIPEA (65 mL, 380 mmol) followed by TBTU (33.59 g, 105 mmol, dissolved in DMF (70 mL)). The reaction mixture is stirred at rt for 2 h before it is poured into water/ice and extracted twice with diethyl ether (2×100 mL). The organic extracts are washed with sat. aq. NaHCO$_3$ solution, 10% aq. citric acid solution and brine, dried over Na$_2$SO$_4$, filtered, evaporated and dried to give 5,5-dimethyl-4,5,6,7-tetrahydro-benzo[c]thiophene-1-carboxylic acid methoxy-methyl-amide (23 g) as a brown oil; LC-MS: t$_R$=1.01 min, [M+1]=254.14.

b) To a solution of diisopropylamine (11.02 g, 109 mmol) in THF (400 mL) is added n-butyl lithium (72.7 mL, 109 mmol, 1.5 M in pentane) at 0-5° C. The solution is cooled to −78° C. and a solution of 5,5-dimethyl-4,5,6,7-tetrahydro-benzo[c]thiophene-1-carboxylic acid methoxy-methyl-amide (23 g, 91 mmol) in THF (100 mL) is added. Upon complete addition, the mixture is stirred for 20 min at −78° C. before a solution of iodine (30 g, 119 mmol) in THF (100 mL) is added. Stirring is continued at −78° C. for 30 min. The reaction is quenched by slowly adding a 1:1 mixture of water/methanol (20 mL). The solution is diluted with water (400 mL) and extracted with diethyl ether (3×100 mL). The combined organic extracts are washed with 10% aq. citric acid solution and brine, dried over Na$_2$SO$_4$, filtered and evaporated. The crude product is purified by CC on silica gel eluting with DCM to afford 3-iodo-5,5-dimethyl-4,5,6,7-tetrahydro-benzo[c]thiophene-1-carboxylic acid methoxy-methyl-amide (18 g) as a brownish oil; LC-MS: t$_R$=1.09 min, [M+1]=380.21.

c) 3-Iodo-5,5-dimethyl-4,5,6,7-tetrahydro-benzo[c]thiophene-1-carboxylic acid methoxy-methyl-amide (18 g, 47 mmol), CuI (14.5 g, 76 mmol) and KF (4.4 g, 76 mmol) are dissolved in DMF (80 mL). The solution is heated to 134° C. and methyl chlorodifluoroacetate (16.26 g, 113 mmol) is added via syringe pump over a period of 4 h. Gas evolution is observed. Upon complete addition, the mixture is cooled and poured into water/ice. The precipitate that forms is collected, suspended in DCM (600 mL), and filtered through a celite pad. The filtrate is washed with 0.5 N aq. HCl (250 mL), followed by sat. aq. NaHCO$_3$ solution, dried over Na$_2$SO$_4$, filtered and evaporated to give 5,5-dimethyl-3-trifluoromethyl-4,5,6,7-tetrahydro-benzo[c]thiophene-1-carboxylic acid methoxy-methyl-amide (14 g) as a brown oil; LC-MS: t$_R$=1.10 min, [M+1]=322.20.

d) A solution of 5,5-dimethyl-3-trifluoromethyl-4,5,6,7-tetrahydro-benzo[c]thiophene-1-carboxylic acid methoxy-methyl-amide (14 g, 44 mmol) in diethyl ether (400 mL) is treated at rt with methyl lithium (80 mL, 1.6 M in diethyl ether). Upon complete addition, the mixture is stirred at rt for 15 min before it is poured onto water/ice and neutralized with aq. HCl. The ether phase is separated and the aq. phase is extracted two more times with diethyl ether (2×100 mL). The organic extracts are washed with brine, dried over MgSO$_4$, filtered and evaporated. The crude product is purified by CC on silica gel eluting with heptane containing 20-30% of DCM to give 1-(5,5-dimethyl-3-trifluoromethyl-4,5,6,7-tetrahydro-benzo[c]thiophen-1-yl)-ethanone (9.1 g) as a yellow oil; LC-MS: t$_R$=1.11 min; [M+1+CH$_3$CN]=318.34; $^1$H NMR (CDCl$_3$): δ 3.04 (t, J=7.0 Hz, 2H), 2.57 (d, J=1.2 Hz, 2H), 2.53 (s, 3H), 1.58 (t, J=7.0 Hz, 2H), 0.99 (s, 6H).

Building Block A

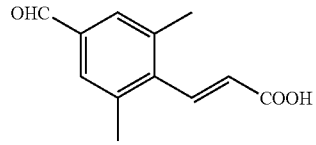

a) To a solution of 4-hydroxy-3,5-dimethyl-benzaldehyde (5.0 g, 33.3 mmol) in DCM (50 mL) and pyridine (8 mL), trifluoromethanesulfonic anhydride (6 mL, 36.6 mmol) is slowly added at 0° C. Upon complete addition, stirring is continued for 2 h at rt. The reaction mixture is diluted with EA and washed three times with water. The separated organic layer is dried over MgSO$_4$, filtered and evaporated. The crude product is purified by CC on silica gel eluting with heptane:EA 4:1 to give trifluoro-methanesulfonic acid 4-formyl-2,6-dimethyl-phenyl ester (5.3 g) as a slightly yellow solid; LC-MS: $t_R$=1.04 min; $^1$H NMR (CDCl$_3$): δ 9.97 (s, 1H), 7.66 (s, 2H), 2.48 (s, 6H).

b) To a stirred solution of trifluoro-methanesulfonic acid 4-formyl-2,6-dimethyl-phenyl ester (4.7 g, 16.7 mmol) in dry DMF (75 mL) under argon is sequentially added at rt triethylamine (3.4 g, 33.3 mmol), methyl acrylate (14.3 g, 167 mmol), 1,3-bis-(diphenylphosphino)-propane (378 mg, 0.92 mmol) and Pd(OAc)$_2$ (187 mg, 0.83 mmol). The mixture is heated to 115° C. and stirred for 5 h. The mixture is diluted with diethyl ether (350 mL) and washed twice with aq. 1 N HCl and once with sat. aq. NaHCO$_3$. The organic extract is dried over MgSO$_4$, filtered and evaporated. The residue is purified by CC on silica gel eluting with heptane:EA 5:1 to give 3-(4-formyl-2,6-dimethyl-phenyl)-acrylic acid methyl ester (2.9 g) as a slightly yellow solid; LC-MS: $t_R$=0.96 min.

c) To a solution of 3-(4-formyl-2,6-dimethyl-phenyl)-acrylic acid methyl ester (2.9 g, 13.3 mmol) in methanol (70 mL), 2 N aq. NaOH (35 mL) is added. The suspension is stirred for 30 min at rt. Methanol is evaporated and the aq. solution is extracted twice with DCM. The aq. layer is acidified with 2 N aq. HCl and extracted twice with EA. The combined EA extracts are dried over MgSO$_4$, filtered and evaporated. The crude product is recrystallized from EA to give 3-(4-formyl-2,6-dimethyl-phenyl)-acrylic acid (2.2 g) as pale yellow crystals; LC-MS: $t_R$=0.83 min; $^1$H NMR (D$_6$-DMSO): δ 12.65 (s br, 1H), 9.92 (s, 1H), 7.66 (d, J=16.4 Hz, 1H), 7.61 (s, 2H), 6.12 (d, J=16.4 Hz, 1H), 2.35 (s, 6H).

Building Block B

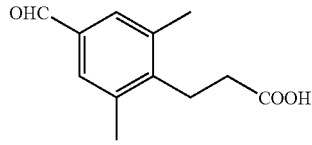

a) To a solution of 3-(4-formyl-2,6-dimethyl-phenyl)-acrylic acid (2.2 g, 10.8 mmol) and DIPEA (2.0 mL, 11.9 mmol) in ethanol (80 mL), Pd/C (200 mg, 10% Pd, moistened with 50% water) is added. The suspension is vigorously stirred under 1 bar of H$_2$ for 1 h. The mixture is filtered over Celite and the filtrate is evaporated. The residue is poured onto 1 N aq. HCl/ice and extracted with EA. The organic extract is washed once with 1 N aq. HCl and once with brine, dried over MgSO$_4$, filtered and evaporated to give 3-(4-hydroxymethyl-2,6-dimethyl-phenyl)-propionic acid (2.2 g) as a pale yellow resin; LC-MS: $t_R$=0.71 min.

b) To a solution of 3-(4-hydroxymethyl-2,6-dimethyl-phenyl)-propionic acid (960 mg, 4.6 mmol) in acetic acid (20 mL), MnO$_2$ (1440 mg, 16.6 mmol) is added. The mixture is stirred at 80° C. for 4.5 h before it is filtered. The filtrate is evaporated and the crude product is purified by CC on silica gel eluting with DCM containing 8% of methanol to give 3-(4-formyl-2,6-dimethyl-phenyl)-propionic acid (800 mg) as a beige solid; LC-MS: $t_R$=0.81 min; $^1$H NMR (D$_6$-DMSO): δ 12.2 (s br, 1H), 9.86 (s, 1H), 7.52 (s, 2H), 2.93-2.85 (m, 2H), 2.38-2.30 (m, 8H).

Building Block C

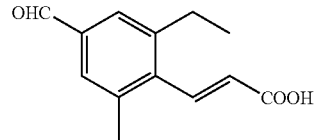

3-(2-Ethyl-4-formyl-6-methyl-phenyl)-acrylic acid is prepared in analogy to Building Block A; LC-MS: $t_R$=0.87 min; $^1$H NMR (CDCl$_3$): δ 9.98 (s, 1H), 7.96 (d, J=16.4 Hz, 1H), 7.62 (s, 1H), 7.59 8s, 1H), 6.13 (d, J=16.4 Hz, 1H), 2.75 (q, J=7.6 Hz, 2H), 2.42 (s, 3H), 1.25 (t, J=7.6 Hz, 3H).

Building Block D

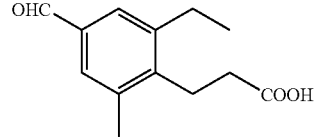

3-(2-Ethyl-4-formyl-6-methyl-phenyl)-propionic acid is prepared in analogy to Building Block B starting from Building Block C; LC-MS: $t_R$=0.86 min; $^1$H NMR (CDCl$_3$): δ 9.93 (s, 1H), 7.58 (s, 1H), 7.53 (s, 1H), 3.11-3.04 (m, 2H), 2.75 (q, J=7.6 Hz, 2H), 2.56-2.50 (m, 2H), 2.43 (s, 3H), 1.28 (t, J=7.6 Hz, 3H).

Intermediate 1

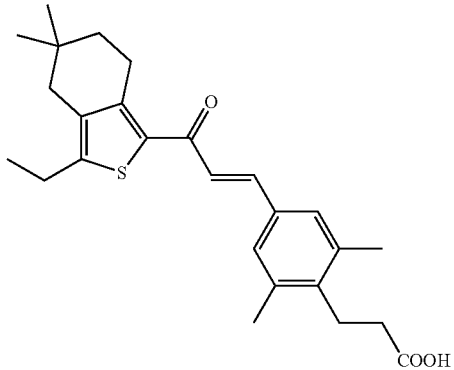

A solution of 1-(3-ethyl-5,5-dimethyl-4,5,6,7-tetrahydro-benzo[c]thiophen-1-yl)-ethanone (400 mg, 1.69 mmol), 3-(4-formyl-2,6-dimethyl-phenyl)-propionic acid (419 mg, 2.03 mmol) and NaOH (1.7 g, 42.5 mmol) in methanol (17 mL) is stirred at 75° C. for 75 min before it is diluted with 1 N aq. HCl and extracted twice with EA. The organic extracts are dried over MgSO$_4$, filtered and evaporated. The crude product is purified by CC on silica gel eluting with DCM containing 6% of methanol to give 3-{4-[3-(3-ethyl-5,5-dimethyl-4,5,6,7-tetrahydro-benzo[c]thiophen-1-yl)-3-oxo-propenyl]-2,6-dimethyl-phenyl}-propionic acid (620 mg) as a pale yellow solid; LC-MS: $t_R$=1.17 min; [M+1]=425.34; $^1$H NMR (CDCl$_3$): δ 7.68 (d, J=15.8 Hz, 1H), 7.28 (s, 2H), 7.27 (d, J=15.8 Hz, 1H), 3.18 (t, J=7.0 Hz, 2H), 3.06-2.98 (m, 2H), 2.78 (q, J=7.6 Hz, 2H), 2.54-2.48 (m, 2H), 2.39 (s, 6H), 2.34 (s, 2H), 1.58 (t, J=7.0 Hz, 2H), 1.32 (t, J=7.6 Hz, 3H).

Intermediate 2A

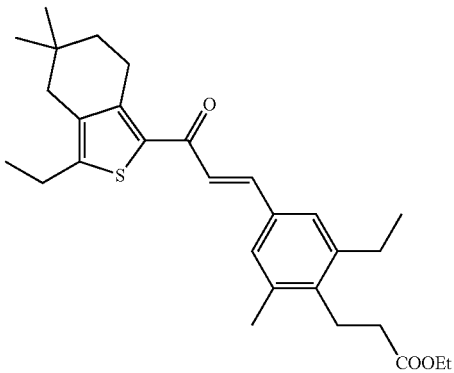

A solution of 1-(3-ethyl-5,5-dimethyl-4,5,6,7-tetrahydro-benzo[c]thiophen-1-yl)-ethanone (143 mg, 0.606 mmol) and 3-(2-ethyl-4-formyl-6-methyl-phenyl)-propionic acid (200 mg, 0.908 mmol) in ethanol (15 mL) is treated with 5 N HCl in isopropanol (3 mL). The dark brown reaction mixture is stirred at rt for 3 h, then at 50° C. for 48 h before DIPEA (4 mL) is added. The solvent is removed in vacuo and the crude product is purified by prep. HPLC (Grom-Sil 120 ODS-4-HE, 30×75 mm, 10 μm, acetonitrile/water (0.5% HCOOH), 10% to 95% acetonitrile) to give 3-{2-ethyl-4-[3-(3-ethyl-5,5-dimethyl-4,5,6,7-tetrahydro-benzo[c]thiophen-1-yl)-3-oxo-propenyl]-6-methyl-phenyl}-propionic acid ethyl ester (157 mg) as a yellow oil; LC-MS: $t_R$=1.27 min, [M+1]=467.43.

Intermediate 2B

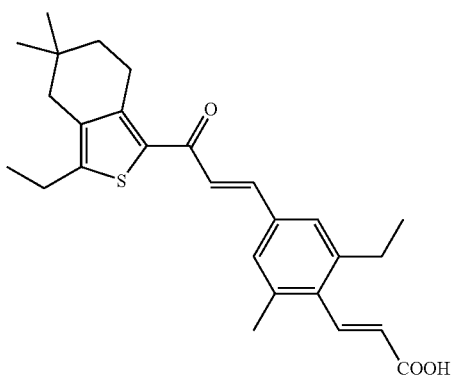

A solution of 1-(3-ethyl-5,5-dimethyl-4,5,6,7-tetrahydro-benzo[c]thiophen-1-yl)-ethanone (200 mg, 0.846 mmol) and 3-(2-ethyl-4-formyl-6-methyl-phenyl)-acrylic acid (203 mg, 0.931 mmol) in methanolic NaOH (8 mL, 10 g NaOH in 100 mL methanol) is stirred at rt for 3 h before it is carefully acidified to pH 1 by adding 2 N aq. HCl. The mixture is extracted twice with DCM and the organic extracts are washed with water and brine, dried over MgSO$_4$, filtered and evaporated. The crude product is crystallised from acetonitrile (40 mL) to give 3-{2-ethyl-4-[3-(3-ethyl-5,5-dimethyl-4,5,6,7-tetrahydro-benzo[c]thiophen-1-yl)-3-oxo-propenyl]-6-methyl-phenyl}-acrylic acid (222 mg) as yellow crystals. From the mother liquor a second crop (29 mg) of product can be obtained after purification by prep. HPLC (Grom-Sil 120 ODS-4-HE, 30×75 mm, 10 μm, acetonitrile/water (0.5% HCOOH), 20% to 95% acetonitrile); LC-MS: $t_R$=1.20 min, [M+1]=437.31.

Intermediate 3

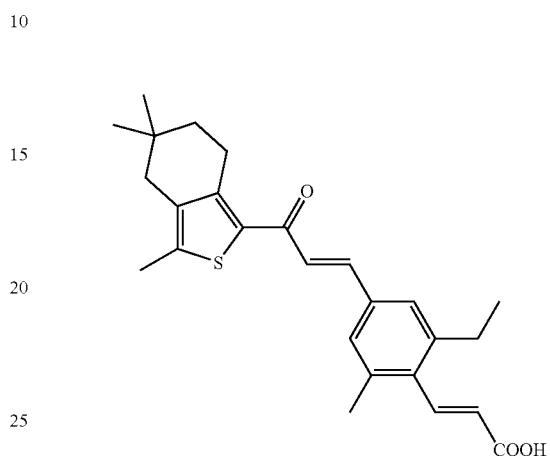

3-{2-Ethyl-6-methyl-4-[3-oxo-3-(3,5,5-trimethyl-4,5,6,7-tetrahydro-benzo[c]thiophen-1-yl)-propenyl]-phenyl}-acrylic acid is prepared from 1-(3,5,5-trimethyl-4,5,6,7-tetrahydro-benzo[c]thiophen-1-yl)-ethanone and 3-(2-ethyl-4-formyl-6-methyl-phenyl)-acrylic acid in analogy to Intermediate 2B; LC-MS: $t_R$=1.17 min; [M+1]=423.34; $^1$H NMR (CDCl$_3$): δ 7.97 (d, J=16.4 Hz, 1H), 7.68 (d, J=15.2 Hz, 1H), 7.33 (s, 2H), 7.28 (d, J=15.8 Hz, 1H), 6.13 (d, J=15.8 Hz, 1H), 3.16 (t, J=7.0 Hz, 2H), 2.77 (q, J=7.6 Hz, 2H), 2.41 (s, 3H), 2.39 (s, 3H), 2.32 (s, 2H), 1.57 (t, J=6.4 Hz, 2H), 1.24 (t, J=7.6 Hz, 3H), 1.00 (s, 6H).

Intermediate 4

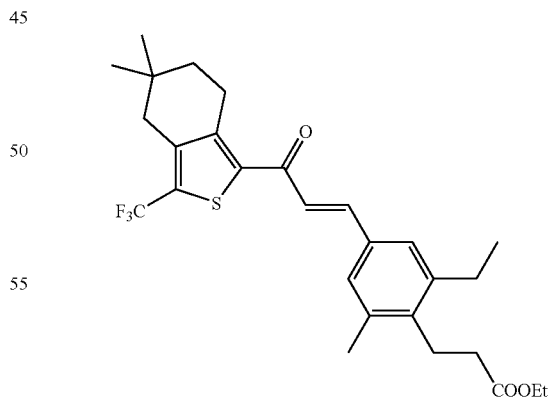

3-{4-[3-(5,5-Dimethyl-3-trifluoromethyl-4,5,6,7-tetrahydro-benzo[c]thiophen-1-yl)-3-oxo-propenyl]-2-ethyl-6-methyl-phenyl}-propionic acid ethyl ester is prepared in analogy to Intermediate 2A starting from Scaffold F and Building Block D; LC-MS: $t_R$=1.29 min, [M+1]=506.68.

Intermediate 5

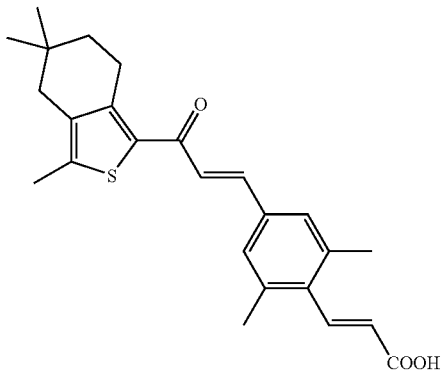

3-{2,6-Dimethyl-4-[3-oxo-3-(3,5,5-trimethyl-4,5,6,7-tetrahydro-benzo[c]thiophen-1-yl)-propenyl]-phenyl}-acrylic acid (570 mg) is obtained by condensing Scaffold D (415 mg, 1.87 mmol) with Building Block B (381 mg, 1.87 mmol) in analogy to Intermediate 2B; LC-MS: $t_R$=1.17 min, [M+1]= 409.21.

Example 1

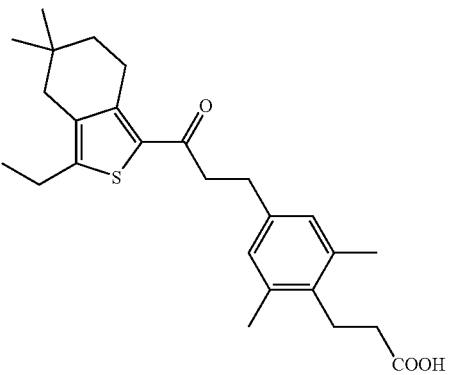

To a solution of 3-{4-[3-(3-ethyl-5,5-dimethyl-4,5,6,7-tetrahydro-benzo[c]thiophen-1-yl)-3-oxo-propenyl]-2,6-dimethyl-phenyl}-propionic acid (610 mg, 1.44 mmol) and DIPEA (204 mg, 1.58 mmol) in ethanol (30 mL) is added Pd/C (300 mg, 10% Pd, moistened with 50% water). The slurry is stirred at rt for 18 h under 1 atm $H_2$. The mixture is filtered and the filtrate is evaporated. The crude product is purified by prep. HPLC (Grom-Sil 120 ODS-4-HE, 30×75 mm, 10 µm, acetonitrile/water (0.5% HCOOH), 20% to 95% acetonitrile) to give 3-{4-[3-(3-ethyl-5,5-dimethyl-4,5,6,7-tetrahydro-benzo[c]thiophen-1-yl)-3-oxo-propyl]-2,6-dimethyl-phenyl}-propionic acid (460 mg) as a colourless lyophilisate; LC-MS: $t_R$=1.15 min; [M+1]=427.40; $^1$H NMR (CDCl$_3$): δ 6.91 (s, 2H), 3.10-2.90 (m, 8H), 2.73 (q, J=7.6 Hz, 2H), 2.53-2.46 (m, 2H), 2.32 (s, 6H), 2.30 (s, 2H), 1.54 (t, J=7.0 Hz, 2H), 1.28 (t, J=7.6 Hz, 3H), 0.97 (s, 6H).

Example 2

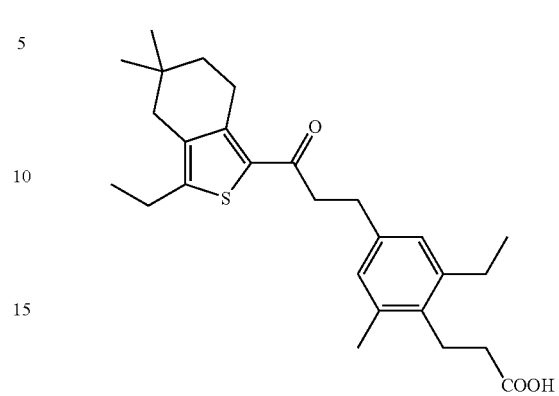

a) To a solution of 3-{2-ethyl-4-[3-(3-ethyl-5,5-dimethyl-4,5,6,7-tetrahydro-benzo[c]thiophen-1-yl)-3-oxo-propenyl]-6-methyl-phenyl}-propionic acid ethyl ester (153 mg, 0.328 mmol) in ethanol, Pd/C (80 mg, 10% Pd, moistened with 50% water) is added and the resulting slurry is stirred at rt for 72 h under 1 bar of $H_2$. The reaction mixture is filtered and the filtrate is evaporated. The crude product is purified by prep. HPLC (Grom-Sil 120 ODS-4-HE, 30×75 mm, 10 µm, acetonitrile/water (0.5% HCOOH), 20% to 95% acetonitrile) to give 3-{2-ethyl-4-[3-(3-ethyl-5,5-dimethyl-4,5,6,7-tetrahydro-benzo[c]thiophen-1-yl)-3-oxo-propyl]-6-methyl-phenyl}-propionic acid ethyl ester (95 mg) as an amorphous solid; LC-MS: $t_R$=1.26 min, [M+1]=469.40.

b) A solution of 3-{2-ethyl-4-[3-(3-ethyl-5,5-dimethyl-4,5,6,7-tetrahydro-benzo[c]thiophen-1-yl)-3-oxo-propyl]-6-methyl-phenyl}-propionic acid ethyl ester (92 mg, 0.196 mmol) in ethanol (2 mL) is treated with 2 N aq. NaOH (2 mL). The solution is stirred at rt for 1 h before the solvent is removed in vacuo. The residue is dissolved in 2 N aq. HCl, and extracted with EA. The organic extract is washed with brine, dried over Na$_2$SO$_4$, filtered and evaproated to give 3-{2-ethyl-4-[3-(3-ethyl-5,5-dimethyl-4,5,6,7-tetrahydro-benzo[c]thiophen-1-yl)-3-oxo-propyl]-6-methyl-phenyl}-propionic acid as an amorphous solid; LC-MS: $t_R$=1.16 min; [M+1]=441.36; $^1$H NMR (CDCl$_3$): δ 6.95 (s, 1H), 6.93 (s, 1H), 3.12-2.94 (m, 8H), 2.74 (q, J=7.6 Hz, 2H), 2.66 (q, J=7.6 Hz, 2H), 2.56-2.48 (m, 2H), 2.36 (s, 3H), 2.32 (s, 2H), 1.56 (t, J=7.0 Hz, 2H), 1.29 (t, J=7.6 Hz, 3H), 1.24 (t, J=7.6 Hz, 3H).

Example 3

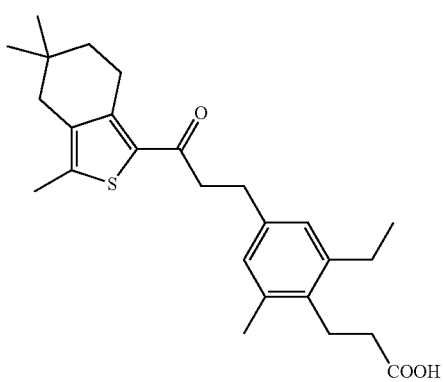

To a solution of 3-{2-ethyl-6-methyl-4-[3-oxo-3-(3,5,5-trimethyl-4,5,6,7-tetrahydro-benzo[c]thiophen-1-yl)-propenyl]-phenyl}-acrylic acid (Intermediate 3; 340 mg, 0.805 mmol) and DIPEA (182 mg, 1.41 mmol) in ethanol, Pd/C (340 mg, 10% Pd, moistened with 50% water) is added and the resulting slurry is stirred at 50° C. for 72 h under 10 bar of H$_2$. Another portion of Pd/C is added and stirring is continued for 16 h at 50° C. under 10 bar of H$_2$. The reaction mixture is filtered and the filtrate is evaporated. The crude product is purified by prep. HPLC (Grom-Sil 120 ODS-4-HE, 30×75 mm, 10 µm, acetonitrile/water (0.5% HCOOH), 20% to 95% acetonitrile) to give 3-{2-ethyl-6-methyl-4-[3-oxo-3-(3,5,5-trimethyl-4,5,6,7-tetrahydro-benzo[c]thiophen-1-yl)-propyl]-phenyl}-propionic acid (154 mg) as a colourless foam; LC-MS: $t_R$=1.15 min, [M+1]=427.30.

Example 4

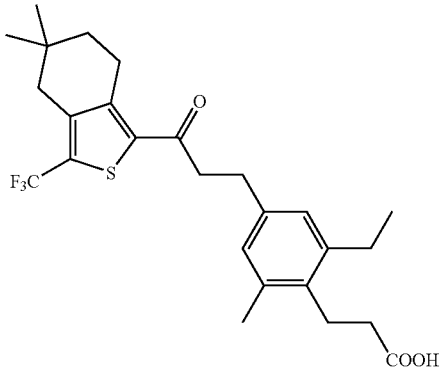

3-{4-[3-(5,5-Dimethyl-3-trifluoromethyl-4,5,6,7-tetrahydro-benzo[c]thiophen-1-yl)-3-oxo-propyl]-2-ethyl-6-methyl-phenyl}-propionic acid is prepared in analogy to Example 2 starting from Intermediate 4; LC-MS: $t_R$=1.17 min, [M+1]=481.36.

Example 5

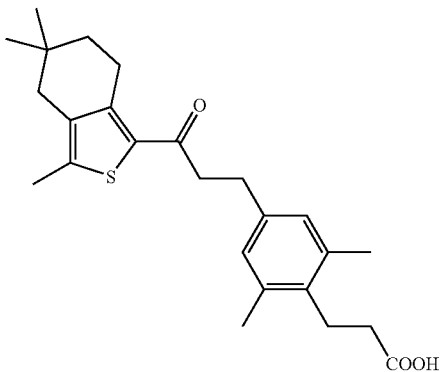

3-{2,6-Dimethyl-4-[3-oxo-3-(3,5,5-trimethyl-4,5,6,7-tetrahydro-benzo[c]thiophen-1-yl)-propyl]-phenyl}-propionic acid (430 mg) is obtained starting from Intermediate 5 (548 mg, 1.34 mmol) in analogy to Example 3; LC-MS: $t_R$=1.13 min; [M+1]=413.34; $^1$H NMR (CDCl$_3$): δ 0.97 (s, 6H), 1.53 (t, J=6.7 Hz, 2H), 2.28 (s, 2H), 2.32 (s, 6H), 2.33 (s, 3H), 2.45-2.54 (m, 2H), 2.89-2.99 (m, 4H), 2.99-3.10 (m, 4H), 6.91 (s, 2H).

Example 6

GTPγS Assay to Determine EC$_{50}$ Values

GTPγS binding assays are performed in 96 well microtiter plates (Nunc, 442587) in a final volume of 200 µl, using membrane preparations of CHO cells expressing recombinant human S1P1 receptor. Assay conditions are 20 mM Hepes (Fluka, 54461), 100 mM NaCl (Fluka, 71378), 5 mM MgCl$_2$ (Fluka, 63064), 0.1% BSA (Calbiochem, 126609), 1 µM GDP (Sigma, G-7127), 2.5% DMSO (Fluka, 41644), 50 pM $^{35}$S-GTPγS (Amersham Biosciences, SJ1320). The pH is 7.4. Test compounds are dissolved and diluted in 100% DMSO and pre-incubated at room temperature for 30 min in 150 µl of the above assay buffer, in the absence of $^{35}$S-GTPγS. After addition of 50 µl of $^{35}$S-GTPγS, the assay is incubated for 1 h at rt. The assay is terminated by transfer of the reaction mixture to a Multiscreen plate (Millipore, MAHFC1H60) using a cell harvester from Packard Biosciences, and the plates are washed with ice-cold 10 mM Na$_2$HPO$_4$/NaH$_2$PO$_4$ (70%/30%), dried, sealed at the bottom and, after addition of 25 µl MicroScint20 (Packard Biosciences, order no. 6013621), sealed on the top. Membrane-bound $^{35}$S-GTPγS is measured with a TopCount from Packard Biosciences.

EC$_{50}$ is the concentration of agonist inducing 50% of the maximal specific $^{35}$S-GTPγS binding. Specific binding is determined by subtracting non-specific binding from maximal binding. Maximal binding is the amount of cpm bound to the Multiscreen plate in the presence of 10 µM of S1P. Non-specific binding is the amount of binding in the absence of an agonist in the assay.

Table 1 shows the EC$_{50}$ value of a compound of the present invention. The EC$_{50}$ value was determined according to the method described above.

TABLE 1

| Compound of Example | EC$_{50}$ [nM] |
| --- | --- |
| 4 | 4.0 |

Example 7

Assessment of in Vivo Efficacy

The efficacy of the compounds of Formula (I) is assessed by measuring the circulating lymphocytes after oral administration of 3 to 30 mg/kg of a compound of Formula (I) to normotensive male Wistar rats. The animals are housed in climate-controlled conditions with a 12 h-light/dark cycle, and have free access to normal rat chow and drinking water. Blood is collected before and 3, 6 and 24 h after drug administration. Full blood is subjected to hematology using Advia Hematology system (Bayer Diagnostics, Zurich, Switzerland).

All data are presented as mean ±SEM. Statistical analyses are performed by analysis of variance (ANOVA) using Statistica (StatSoft) and the Student-Newman-Keuls procedure for multiple comparisons. The null hypothesis is rejected when p<0.05.

As an example, Table 2 shows the effect on lymphocyte counts 6 h after oral administration of 10 mg/kg of a compound of the present invention to normotensive male Wistar rats as compared to a group of animals treated with vehicle only.

TABLE 2

| Compound of Example | Lymphocyte counts |
|---|---|
| 1 | −61 ± 5% |

The invention claimed is:

1. A compound selected from the group consisting of thiophenes of the Formula (I),

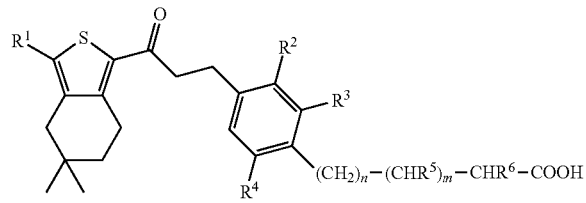

Formula (I)

wherein
R$^1$ represents methyl, trifluoromethyl, or ethyl;
R$^2$ represents hydrogen, C$_{1-4}$-alkyl, methoxy, or halogen;
R$^3$ represents hydrogen, C$_{1-4}$-alkyl, C$_{1-4}$-alkoxy, or halogen;
R$^4$ represents hydrogen, C$_{1-4}$-alkyl, or halogen;
R$^5$ represents hydrogen;
R$^6$ represents hydrogen or hydroxy;
in case R$^6$ represents hydroxy, R$^5$ can in addition represent hydroxy;
n represents 0;
m represents 0 or 1; and
in case m represents 1, n can in addition represent 1;
in free or salt form.

2. The compound according to claim 1, wherein R$^1$ represents an ethyl group.

3. The compound according to claim 1, wherein R$^1$ represents a methyl group.

4. The compound according to claim 1, wherein R$^1$ represents a trifluoromethyl group.

5. The compound according to claim 1, wherein R$^2$ represents a methoxy group, and R$^3$ and R$^4$ represent hydrogen.

6. The compound according to claim 1, wherein R$^2$ represents hydrogen, and R$^3$ and R$^4$ represent C$_{1-4}$-alkyl.

7. The compound according to claim 6, wherein R$^3$ and R$^4$ represent a methyl group.

8. The compound according to claim 6, wherein R$^3$ and R$^4$ represent an ethyl group.

9. The compound according to claim 6, wherein R$^3$ represents a methyl group, and R$^4$ represents an ethyl group.

10. The compound according to claim 1, wherein R$^2$ represents hydrogen, R$^3$ represents a methoxy group, and R$^4$ represents a chlorine atom.

11. The compound according to claim 1, wherein R$^2$ represents hydrogen, R$^3$ represents a methyl group, and R$^4$ represents a chlorine atom.

12. The compound according to claim 1, wherein R$^5$ and R$^6$ represent hydrogen.

13. The compound according to claim 12, wherein n represents 0, and m represents 1.

14. The compound according to claim 12, wherein n represents 1, and m represents 1.

15. The compound according to claim 1, wherein m represents 1, and R$^5$ and R$^6$ represent hydroxy.

16. The compound according to claim 15, wherein n represents 0.

17. The compound according to claim 1, wherein R$^5$ represents hydrogen, and R$^6$ represents hydroxy.

18. The compound according to claim 1 selected from the group consisting of:
3-{4-[3-(3-ethyl-5,5-dimethyl-4,5,6,7-tetrahydro-benzo[c]thiophen-1-yl)-3-oxo-propyl]-2,6-dimethyl-phenyl}-propionic acid;
3-{4-[3-(5,5-dimethyl-3-trifluoromethyl-4,5,6,7-tetrahydro-benzo[c]thiophen-1-yl)-3-oxo-propyl]-2-ethyl-6-methyl-phenyl}-propionic acid;
3-{2-ethyl-6-methyl-4-[3-oxo-3-(3,5,5-trimethyl-4,5,6,7-tetrahydro-benzo[c]thiophen-1-yl)-propyl]-phenyl}-propionic acid; and
3-{2-ethyl-4-[3-(3-ethyl-5,5-dimethyl-4,5,6,7-tetrahydro-benzo[c]thiophen-1-yl)-3-oxo-propyl]-6-methyl-phenyl}-propionic acid.

19. The compound according to claim 1 which is 3-{2,6-dimethyl-4-[3-oxo-3-(3,5,5-trimethyl-4,5,6,7-tetrahydro-benzo[c]thiophen-1-yl)-propyl]-phenyl}-popionic acid.

20. A pharmaceutical composition comprising a compound according to claim 1 in free or pharmaceutically salt form, and a pharmaceutically acceptable carrier.

21. A compound selected from the group consisting of thiophenes of Formula (II)

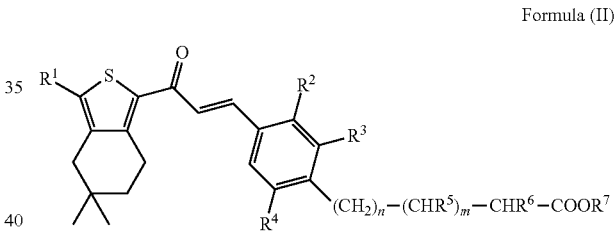

Formula (II)

wherein R$^1$, R$^2$, R$^3$, R$^4$, R$^5$, R$^6$, n and m are as defined in claim 1 for Formula (I), and
R$^7$ represents hydrogen, methyl, ethyl, or tert-butyl;
in free or salt form.

22. A compound selected from the group consisting of thiophenes of Formula (III)

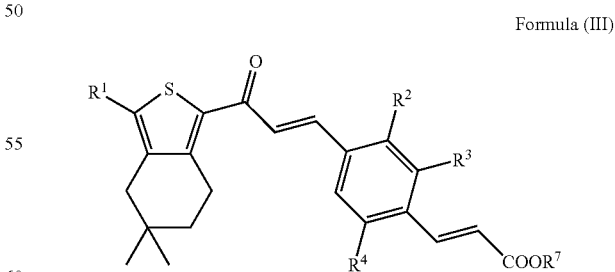

Formula (III)

wherein R$^1$, R$^2$, R$^3$, and R$^4$ are as defined in claim 1 for Formula (I), and
R$^7$ represents hydrogen, methyl, ethyl, or tert-butyl;
in free or salt form.

23. The compound according to claim 2, wherein R$^2$ represents a methoxy group, and R$^3$ and R$^4$ represent hydrogen.

24. The compound according to claim 3, wherein $R^2$ represents a methoxy group, and $R^3$ and $R^4$ represent hydrogen.

25. The compound according to claim 4, wherein $R^2$ represents a methoxy group, and $R^3$ and $R^4$ represent hydrogen.

26. The compound according to claim 2, wherein $R^2$ represents hydrogen, and $R^3$ and $R^4$ represent $C_{1-4}$-alkyl.

27. The compound according to claim 3, wherein $R^2$ represents hydrogen, and $R^3$ and $R^4$ represent $C_{1-4}$-alkyl.

28. The compound according to claim 4, wherein $R^2$ represents hydrogen, and $R^3$ and $R^4$ represent $C_{1-4}$-alkyl.

29. The compound according to claim 2, wherein $R^2$ represents hydrogen, $R^3$ represents a methoxy group, and $R^4$ represents a chlorine atom.

30. The compound according to claim 3, wherein $R^2$ represents hydrogen, $R^3$ represents a methoxy group, and $R^4$ represents a chlorine atom.

31. The compound according to claim 4, wherein $R^2$ represents hydrogen, $R^3$ represents a methoxy group, and $R^4$ represents a chlorine atom.

32. The compound according to claim 2, wherein $R^2$ represents hydrogen, $R^3$ represents a methyl group, and $R^4$ represents a chlorine atom.

33. The compound according to claim 3, wherein $R^2$ represents hydrogen, $R^3$ represents a methyl group, and $R^4$ represents a chlorine atom.

34. The compound according to claim 4, wherein $R^2$ represents hydrogen, $R^3$ represents a methyl group, and $R^4$ represents a chlorine atom.

* * * * *